United States Patent
Muddiman et al.

(10) Patent No.: US 11,370,812 B2
(45) Date of Patent: Jun. 28, 2022

(54) MATERIALS AND METHODS FOR DETECTION AND QUANTIFICATION OF β-N-METHYLAMINO-L-ALANINE

(71) Applicant: NORTH CAROLINA STATE UNIVERSITY, Raleigh, NC (US)

(72) Inventors: David C. Muddiman, Apex, NC (US); Philip L. Loziuk, Raleigh, NC (US); Joshua G. Pierce, Raleigh, NC (US); Gavin Williams, Raleigh, NC (US); Yasamin Moazami, Seattle, WA (US)

(73) Assignee: North Carolina State University, Raleigh, NC (US)

( * ) Notice: Subject to any disclaimer, the term of this patent is extended or adjusted under 35 U.S.C. 154(b) by 525 days.

(21) Appl. No.: 16/321,091

(22) PCT Filed: Jul. 31, 2017

(86) PCT No.: PCT/US2017/044702
§ 371 (c)(1),
(2) Date: Jan. 28, 2019

(87) PCT Pub. No.: WO2018/023116
PCT Pub. Date: Feb. 1, 2018

(65) Prior Publication Data
US 2019/0161515 A1 May 30, 2019

Related U.S. Application Data

(60) Provisional application No. 62/368,437, filed on Jul. 29, 2016, provisional application No. 62/368,562, filed on Jul. 29, 2016.

(51) Int. Cl.
*G01N 33/68* (2006.01)
*C07K 1/13* (2006.01)
(Continued)

(52) U.S. Cl.
CPC .............. *C07K 1/13* (2013.01); *C07B 59/008* (2013.01); *C07C 229/26* (2013.01); *C07K 14/00* (2013.01);
(Continued)

(58) Field of Classification Search
CPC ............ G01N 33/6812; G01N 33/6848; C07B 59/008; C07K 1/13
See application file for complete search history.

(56) References Cited

U.S. PATENT DOCUMENTS

2012/0258886 A1* 10/2012 Marto .................. C07D 207/40
506/15

OTHER PUBLICATIONS

Downing, S. et al. "Nitrogen starvation of cyanobacteria results in the production of b-N-methylamino-L-alanine," Toxicon 58 (2011) 187-194. (Year: 2011).*
Downing, S. et al. "The fate of the cyanobacterial toxin β-N-methylamino-L-alanine in freshwater mussels," Ecotoxicology and Environmental Safety 101 (2014) 51-58 (Year: 2014).*
(Continued)

*Primary Examiner* — Jennifer Wecker
*Assistant Examiner* — Michelle Adams
(74) *Attorney, Agent, or Firm* — Meunier Carlin & Curfman LLC

(57) ABSTRACT

Provided herein are isotopically labeled reagents, including isotopically labeled small molecules and peptides, that can be used to detect and/or quantify β-N-methylamino-L-alanine (BMAA) in a sample. The reagents can be used as stable isotope labeled standards in analytical methods, including in conjunction with mass spectrometry, to detect and/or quantify BMAA in a sample, such as a protein sample from a subject.

11 Claims, 14 Drawing Sheets

(51) Int. Cl.
  *C07B 59/00* (2006.01)
  *C12N 9/02* (2006.01)
  *C07K 14/00* (2006.01)
  *C07C 229/26* (2006.01)
  *G01N 33/52* (2006.01)
  *G01N 33/573* (2006.01)

(52) U.S. Cl.
  CPC ........... *C12N 9/0089* (2013.01); *G01N 33/52* (2013.01); *G01N 33/573* (2013.01); *G01N 33/6812* (2013.01); *G01N 33/6848* (2013.01); *C12Y 115/01001* (2013.01); *G01N 2800/2835* (2013.01)

(56) References Cited

OTHER PUBLICATIONS

International Search Report and Written Opinion in PCT/US2017/044702, dated Oct. 26, 2017. 8 pages.
International Search Report and Written Opinion in PCT/US2017/044693, dated Nov. 2, 2017. 8 pages.
Reece, Deborah M. et al. "Synthesis of 14C-L-a amino-B-methylaminopropionic acid and its metabolism in the rat" Biochemical Society Transactions, 1989, 17(1), pp. 203-204.
Hu, Yulin et al. "Synthesis and optical resolution of the neurotoxin 2-amino-3-([15N]-methylamino)propanoic acid (BMAA)" Journal of Labelled Compounds and Radiopharmaceuticals, 1990, vol. XXVIII, No. 5, pp. 581-586.

* cited by examiner

H₂N –DGVADVSIEDSVISLSGDHCIIGR*- COOH
|
HPO₃
*C-terminal Arginine is isotopically labeled ($^{13}C_6$, $^{15}N_4$)
Add 0.1M Ba(OH)₂ and 1M Methylamine. Adjust pH to 12.5. React 5 μL (5μg) of peptide with 20 μL of derivatization solution and incubate at 37°C for two hours.
There is a mass change of -66.9348 Da
DGVADVSIEDSVISLBGDHCIIGR*
The B here represents Beta-N-Methylamino L-Alanine
FIG. 1

FIG. 6

*HIGH MASS MEASUREMENT ACCURACY IDENTIFICATION OF ENDOGENOUS BMAA PEPTIDE*

Endogenous BMAA containing peptide from Erythrocytes of sALS Patient DGVADVSIEDSVISLBGDHCIIGR

B = Beta-N-Methylamino-L-Alanine

843.1258 z=3

+1.2 ppm MMA
Theo 843.0867 m/z → 843.0877 z=3

843.3993 z=3

Relative Abundance m/z

FIG. 8

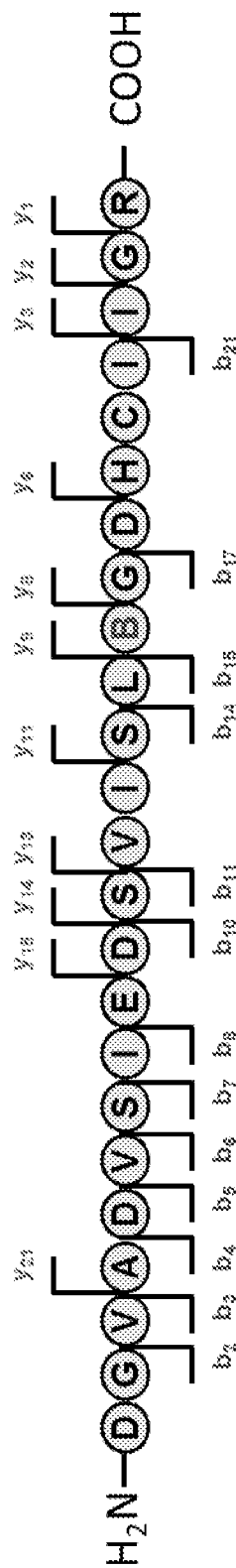
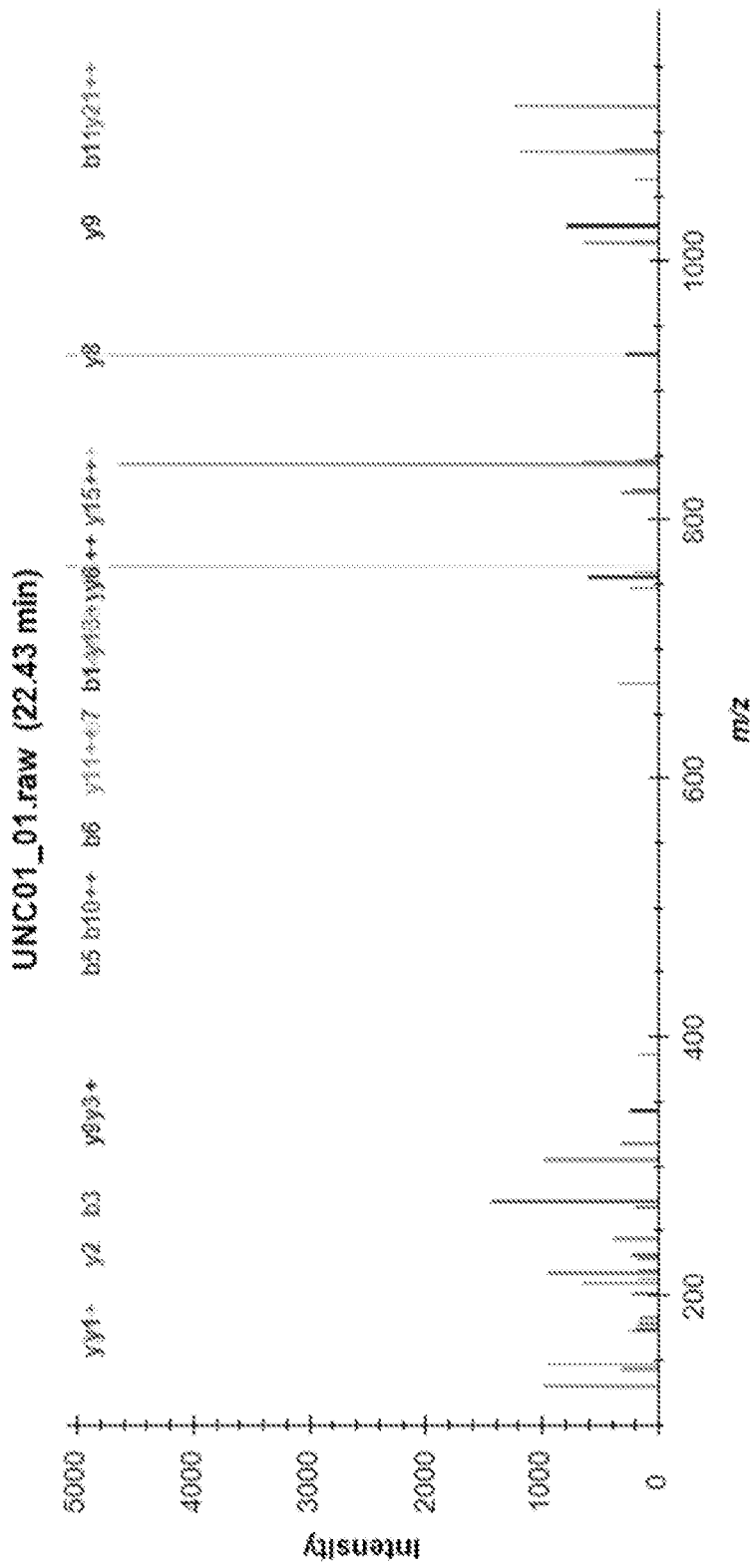
FIG. 10

FIG. 12

Occupancy of BMAA reflecting chemical conversion of Serine to BMAA on 3 peptides, across 5 potential reaction sites.

Peptides:
- RELEELNVPGEIVESLSSSEESITRINKKIEKFQSEEQQTEDELQDKIHPFAQTQSLVY
- PFPGPIPNSLPQNIPPLTQTPVVVPPFLQPEVMGVSKVKEAMAPKHKEMPFPKYPVEPFT
- ESQSLTLTDVENLHLPLPLLQSWMHQPHQPLPPTVMFPPQSVLSLSQSKVLPVPQKAVPY
- PQRDMPIQAFLLYQEPVLGPVRGPFFIIV Reaction site conditions (x-axis, left to right):
1. 1×SER→BMAA [S]; 3×Phospho [S18; S] — RELEELNVPGEIVESLSSSEESITR
2. 2×SER→BMAA [S]; 2×Phospho [S] — RELEELNVPGEIVESLSSSEESITR
3. 3×SER→BMAA [S18; S]; 1×Phospho [S] — RELEELNVPGEIVESLSSSEESITR
4. 1×SER→BMAA [S3] — FQSEEQQTEDELQDK
5. 1×SER→BMAA [S7] — KIEKFQSEEQQTEDELQDK Y-axis: Occupancy (0 to 1)

MATERIALS AND METHODS FOR DETECTION AND QUANTIFICATION OF β-N-METHYLAMINO-L-ALANINE

CROSS REFERENCE TO RELATED APPLICATIONS

This application claims the benefit of U.S. Provisional Patent Application Ser. No. 62/368,437, filed Jul. 29, 2016, and U.S. Provisional Patent Application Ser. No. 62/368,562, filed Jul. 29, 2016, both of which are expressly incorporated herein by reference.

BACKGROUND

The non-protein amino acid β-N-Methylamino-L-Alanine (BMAA) is biosynthetically produced in cyanobacteria. Human exposure to this unnatural amino acid has been linked to neurological disorders, including amyotrophic lateral sclerosis (ALS) and parkinsonism dementia complex (PDC) like symptoms. Dietary exposure of BMAA in primates has shown neurofibrillary tangles (NFT) and β-amyloid plaques, hallmark signs of neuropathological disease. Additionally, cell culture studies have shown that exogenous exposure to BMAA can result in incorporation of this non-protein amino acid in place of L-serine. Supplemental treatment with L-serine has been shown to reduce the rate of BMAA incorporation and regression of neuropathological symptoms.

While these findings suggest that BMAA can be incorporated into proteins, efforts to further study the role of BMAA in biological systems has been hampered by the limited availability of suitable analytical probes and methods. Improved analytical tools and methods are needed to fully understand the qualitative and quantitative nature of incorporation of BMAA in proteins, particularly human proteins, as well as the mechanism and functional consequences of this process.

SUMMARY

Provided herein are isotopically labeled reagents, including isotopically labeled small molecules and peptides, that can be used to detect and/or quantify β-N-methylamino-L-alanine (BMAA) in a sample. The reagents can be used as stable isotope labeled standards in analytical methods, including in conjunction with mass spectrometry, to detect and/or quantify BMAA in a sample, such as a protein sample from a subject.

For example, provided herein are compositions that comprise an isotopically labeled compound defined by the formula below

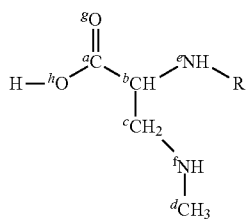

where R represents hydrogen or an amine protecting group, and at east two of $^aC$, $^bC$, $^cC$, $^dC$, $^eN$, $^fN$, $^gO$, and $^hO$ are isotopically labeled with a stable isotope ($^{13}C$, $^{15}N$, and/or $^{18}O$). In certain cases, R is hydrogen. In other cases, R represents an amine protecting group, such as a 9-fluorenylmethyloxycarbonyl group. The isotopically labeled compound can comprise at least 0.5% by weight of the composition.

In some embodiments, at least three (e.g., at least four, at least five, or at least six) of $^aC$, $^bC$, $^cC$, $^dC$, $^eN$, $^fN$, $^gO$, and $^hO$ are isotopically labeled with a stable isotope. In some cases, at least two (e.g., at least three, or at least four) of $^aC$, $^bC$, $^cC$, $^dC$, $^eN$, and $^fN$ are isotopically labeled with a stable isotope. In certain cases, all of $^aC$, $^bC$, $^cC$, $^dC$, $^eN$, and $^fN$ are isotopically labeled with a stable isotope.

In some embodiments, the isotopically labeled compound can be defined by the formula below

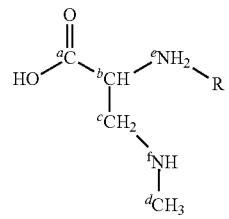

where R represents hydrogen or an amine protecting group (e.g., a 9-fluorenylmethyloxycarbonyl group); the $^{13}C$ isotopic enrichment factor for $^aC$, $^bc$, $^cC$, and $^dC$ is at least 25; and the $^{15}N$ isotopic enrichment factor for $^eN$ and $^fN$ is at least 100. In certain embodiments, the $^{13}C$ isotopic enrichment factor for $^aC$, $^bC$, $^cC$, and $^dC$ can be at least 80 and the $^{15}N$ isotopic enrichment factor for $^eN$ and $^fN$ can be at least 200.

Compositions comprising a polypeptide that includes one or more isotopically labeled β-N-methylamino-L-alanine (BMAA) residues are also provided herein. The isotopically labeled polypeptide can comprise at least 0.5% by weight of the composition. Each of the one or more isotopically labeled BMAA residues can be isotopically labeled with one or more (e.g., two or more) stable isotopes. For example, each of the one or more isotopically labeled BMAA residues can be defined by the formula below

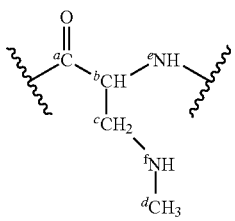

where the $^{13}C$ isotopic enrichment factor for $^dC$ is at least 25; and the $^{15}N$ isotopic enrichment factor for $^fN$ is at least 100. In some cases, the $^{13}C$ isotopic enrichment factor for $^dC$ is at least 80 and the $^{15}N$ isotopic enrichment factor for $^fN$ is at least 200. In some cases, the $^{13}C$ isotopic enrichment factor for $^aC$, $^bC$, and $^cC$ can be at least 25 (e.g., at least 80). In some cases, the $^{15}N$ isotopic enrichment factor for $^eN$ can be at least 100 (e.g., at least 200). In some embodiments, the polypeptide can include a single isotopically labeled β-N-methylamino-L-alanine (BMAA) residue. In other embodiments, the polypeptide can include two or more isotopically labeled BMAA residues (e.g., three or more isotopically labeled BMAA residues, four or more isotopically labeled BMAA residues, five or more isotopically labeled BMAA residues, or ten or more isotopically labeled BMAA residues).

In some embodiments, the polypeptide can be defined by the formula below

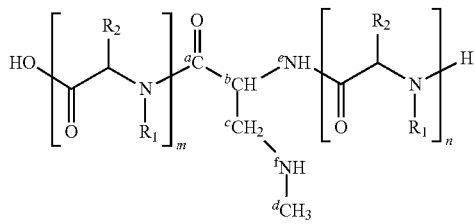

where m is an integer from 0 to 300 and n is an integer from 0 to 300, with the proviso that at least one of m and n is not 0; the $^{13}$C isotopic enrichment factor for $^d$C is at least 25; the $^{15}$N isotopic enrichment factor for $^f$N is at least 100; and independently for each occurrence in the polypeptide, $R_1$ is H and $R_2$ is selected from one of the following

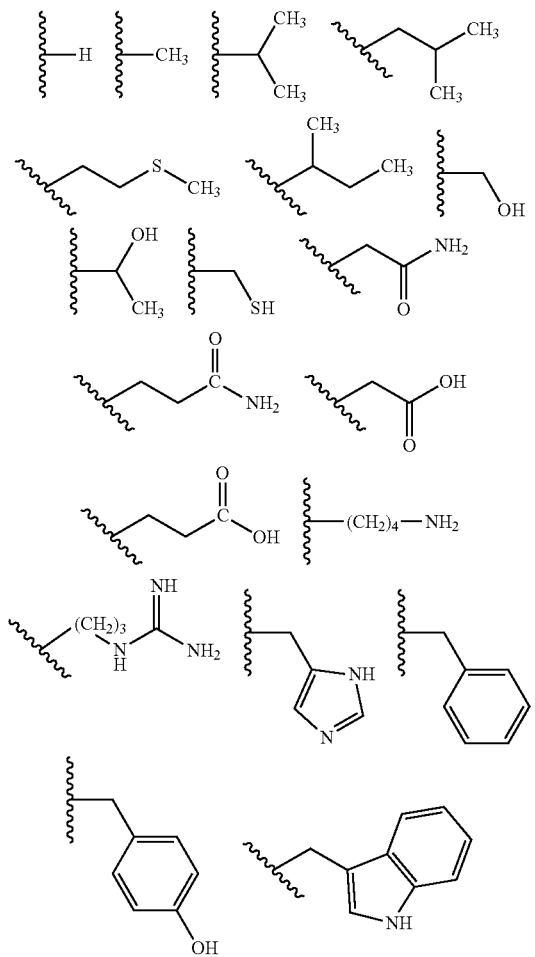

or $R_1$ and $R_2$, together with the atoms to which they are attached, form a five-membered heterocycle defined by the structure below

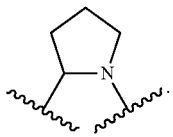

In some embodiments, the $^{13}$C isotopic enrichment factor for $^d$C is at least 80 and the $^{15}$N isotopic enrichment factor for $^f$N is at least 200. In some embodiments, the sum of m and n is from 1 to 50 (e.g., from 1 to 30). In some embodiments, the $^{13}$C isotopic enrichment factor for $^a$C, $^b$C, and $^c$C is at least 25 (e.g., at least 80). In some embodiments, the $^{15}$N isotopic enrichment factor for $^e$N is at least 100 (e.g., at least 200).

The isotopically labeled reagents and compositions described herein can be used in a variety of analytical methods to detect and/or quantify BMAA, such as to detect and/or quantify BMAA in a biological sample such as a protein sample. For example, provided herein are methods for quantifying the amount of BMAA in a sample that comprise: (i) analyzing a test sample by mass spectrometry; (ii) spiking the test sample with a defined amount of an isotopically labeled compound defined by the formula below

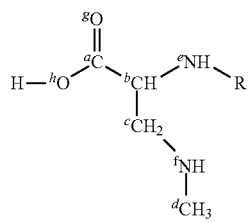

where R represents hydrogen or an amine protecting group, and at least three of $^a$C, $^b$c, $^c$C, $^d$C, $^e$N, $^f$N, $^g$O, and $^h$O are isotopically labeled with a stable isotope; to provide a BMAA-spiked sample; (iii) analyzing the BMAA-spiked sample by mass spectrometry; and (iv) determining the amount of BMAA in the test sample by isotope dilution analysis. Methods can further comprise preparing the test sample, the BMAA-spiked sample, or a combination thereof for analysis by mass spectrometry. For example, the test sample, the BMAA-spiked sample, or a combination thereof can be prepared for analysis by mass spectrometry by a method comprising chemical reactions with flight enhancers, chemical fragmentation, enzymatic digestion, purification, or a combination thereof.

Also provided are methods for incorporating an isotopically-labeled β-N-methylamino-L-alanine (BMAA) residue into a protein or peptide. Methods can comprise providing a protein or peptide that includes a phosphoserine residue; reacting the protein or peptide to convert the phosphoserine residue to an α,β-unsaturated amino acid residue; and reacting the α,β-unsaturated amino acid residue with methylamine to provide a BMAA residue, wherein the methylamine is isotopically enriched with one or more stable isotopes. The methylamine can have a $^{13}$C isotopic enrichment factor of at least 25 (e.g., at least 80) and an $^{15}$N isotopic enrichment factor of at least 100 (e.g., at least 200).

DESCRIPTION OF DRAWINGS

FIG. 1 is and illustration of an example procedure used to convert a phosphoserine-containing peptide to BMAA-containing peptide. The peptide sequence shown in FIG. 1 is unique to superoxide dismustase 1 (SOD1).

Figure 6:
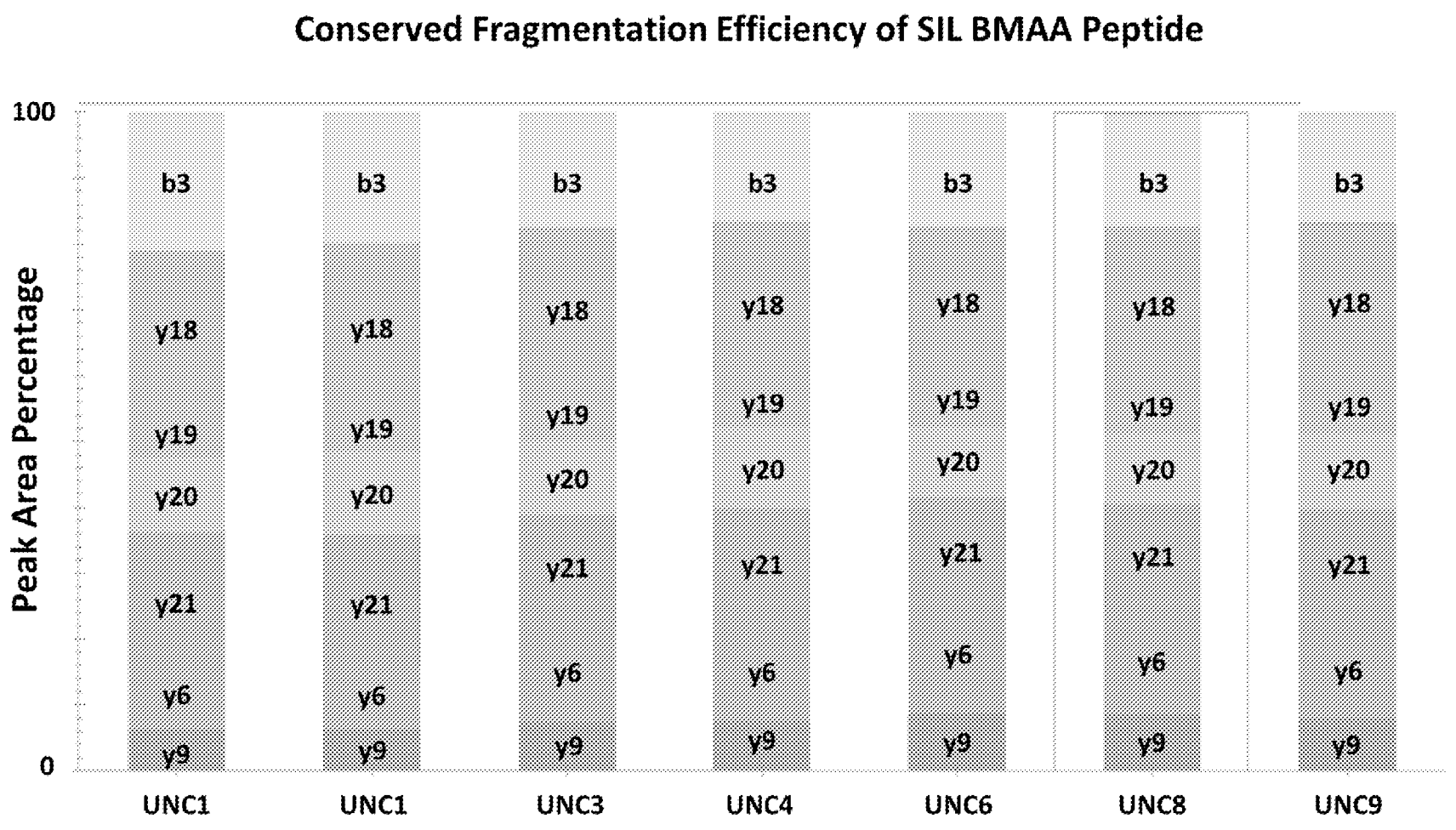

FIG. 6 illustrates the conserved peak area of fragments specific to SIL BMAA peptide that allow for confident identification of endogenous peptide.

FIG. 8 demonstrates the ability of mass spectrometry to accurately identify endogenous BMAA-containing peptide in SOD1 protein digest obtained from ALS erythrocytes.

FIG. 10 illustrates the tandem mass spectrum of BMAA containing stable isotope-label ($^{13}C_3^{15}N_2$ β-N-Methyl-amino-L-Alanine).

FIG. 12 shows the occupancy or abundance of BMAA normalized to the total (phosphorylated+BMAA) after chemical conversion of serine to BMAA on 3 peptides, across 5 potential reaction sites on Beta Casein.

DETAILED DESCRIPTION

Figure 2A:
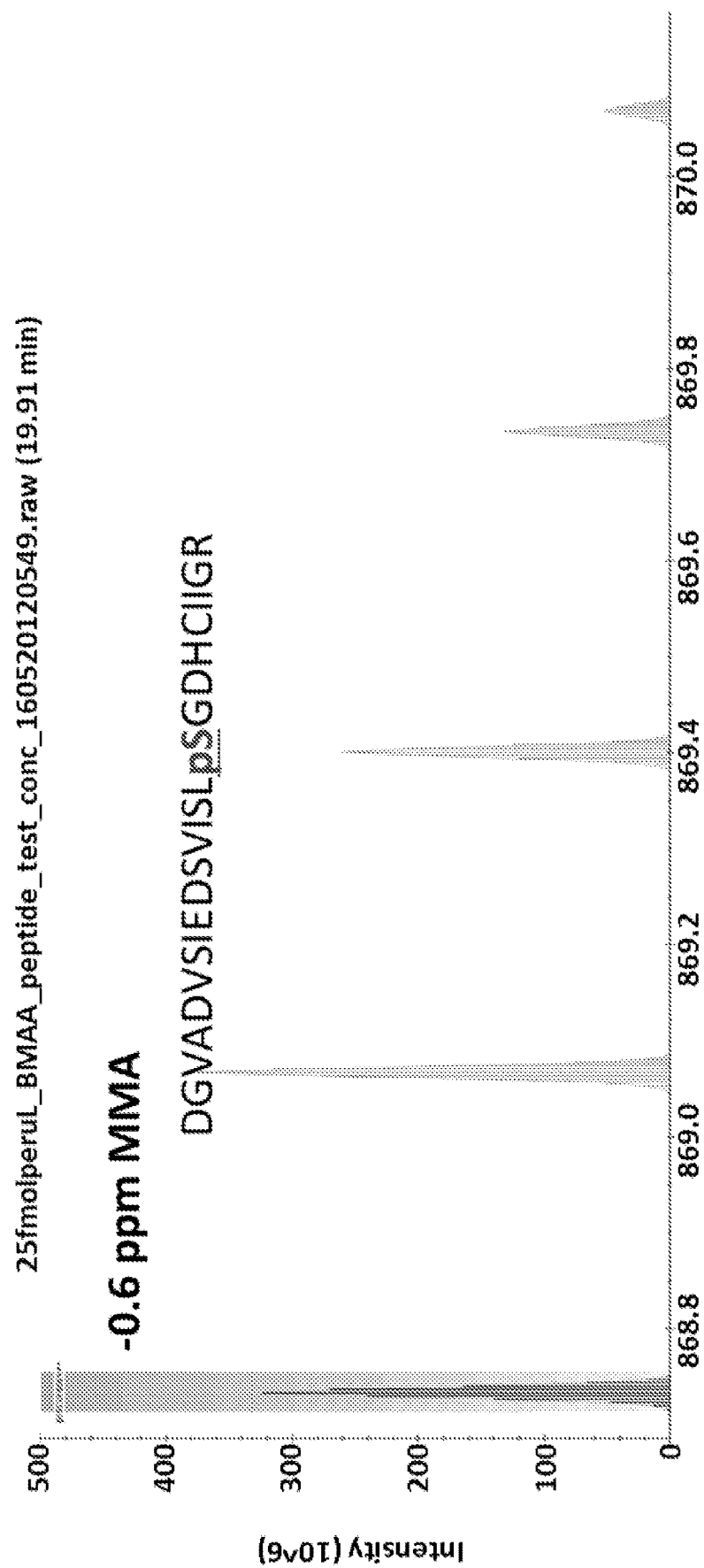
FIGS. 2A and 2B illustrate the intact mass of stable isotope-labeled (SIL) phosphopeptide substrate and BMAA peptide product.

Provided herein are isotopically labeled reagents, including isotopically labeled small molecules and peptides, that can be used to detect and/or quantify β-N-methylamino-L-alanine (BMAA) in a sample. The reagents can be used as stable isotope labeled standards in analytical methods, including in conjunction with mass spectrometry, to detect and/or quantify BMAA in a sample, such as a protein sample from a subject. The reagents can also be used as stable isotope labeled standards in analytical methods, including in conjunction with mass spectrometry, to detect and/or quantify free BMAA in, for example, an environmental sample.

Compositions

Provided herein are compositions that comprise an isotopically labeled compound defined by the formula below

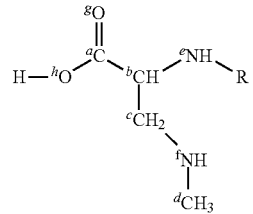

where R represents hydrogen or an amine protecting group, and at least two of $^aC$, $^bC$, $^cC$, $^dC$, $^eN$, $^fN$, $^gO$, and $^hO$ are isotopically labeled with a stable isotope (i.e., $^{13}C$, $^{15}N$, and/or $^{18}O$).

In some embodiments, at least three (e.g., at least four, at least five, at least six, at least seven, or all eight) of $^aC$, $^bC$, $^cC$, $^dC$, $^eN$, $^fN$, $^gO$, and $^hO$ are isotopically labeled with a stable isotope. In certain embodiments, at least two (e.g., at least three, at least four, at least five, or all six) of $^aC$, $^bC$, $^cC$, $^dC$, $^eN$, and $^fN$ are isotopically labeled with a stable isotope. In particular embodiments, all of $^aC$, $^bC$, $^cC$, $^dC$, $^eN$, and $^fN$ are isotopically labeled with a stable isotope.

In some embodiments, the isotopically labeled compound can be defined by the formula below

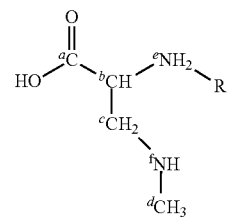

where R represents hydrogen or an amine protecting group; the $^{13}C$ isotopic enrichment factor for $^aC$, $^bC$, $^cC$, and $^dC$ is at least 25; and the $^{15}N$ isotopic enrichment factor for $^eN$ and $^fN$ is at least 100.

The term "isotopic enrichment factor," as used herein, refers to the ratio between the isotopic abundance (e.g., $^{13}C$, $^{15}N$, or $^{18}O$) at a specified position in a compound and the naturally occurring abundance of that isotope. The naturally occurring abundance of $^{13}C$ is 1.1%. The naturally occurring abundance of $^{15}N$ is 0.37%. The naturally occurring abundance of $^{18}O$ is 0.204%.

In some embodiments, the $^{13}C$ isotopic enrichment factor for $^aC$, $^bC$, $^cC$, and $^dC$ is at least 25 (27.5% $^{13}C$ incorporation at each position), at least 30 (33% $^{13}C$ incorporation at each position), at least 35 (38.5% $^{13}C$ incorporation at each position), at least 40 (44% $^{13}C$ incorporation at each position), at least 45 (49.5% $^{13}C$ incorporation at each position), at least 50 (55% $^{13}C$ incorporation at each position), at least 55 (60.5% $^{13}C$ incorporation at each position), at least 60 (66% $^{13}C$ incorporation at each position), at least 65 (71.5% $^{13}C$ incorporation at each position), at least 70 (77% $^{13}C$ incorporation at each position), at least 75 (82.5% $^{13}C$ incorporation at each position), at least 80 (88% $^{13}C$ incorporation at each position), at least 85 (93.5% $^{13}C$ incorporation at each position), or at least 90 (99% $^{13}C$ incorporation at each position).

In some embodiments, the $^{15}$N isotopic enrichment factor for $^eN$ and $^fN$ is at least 100 (37% $^{15}$N incorporation at each position), at least 110 (40.7% $^{15}$N incorporation at each position), at least 120 (44.4% $^{15}$N incorporation at each position), at least 130 (48.1% $^{15}$N incorporation at each position), at least 140 (51.8% $^{15}$N incorporation at each position), at least 150 (55.5% $^{15}$N incorporation at each position), at least 160 (59.2% $^{15}$N incorporation at each position), at least 170 (62.9% $^{15}$N incorporation at each position), at least 180 (66.6% $^{15}$N incorporation at each position), at least 190 (70.3% $^{15}$N incorporation at each position), at least 200 (74% $^{15}$N incorporation at each position), at least 210 (77.7% $^{15}$N incorporation at each position), at least 220 (81.4% $^{15}$N incorporation at each position), at least 230 (85.1% $^{15}$N incorporation at each position), at least 240 (88.8% $^{15}$N incorporation at each position), at least 250 (92.5% $^{15}$N incorporation at each position), at least 260 (96.2% $^{15}$N incorporation at each position), or at least 265 (98.05% $^{15}$N incorporation at each position).

In certain cases, R is hydrogen. In other embodiments, R represents an amine protecting group. Amine protecting groups are well known in the art, and include, for example, carbobenzyloxy (CBZ) groups, p-methoxybenzyl carbonyl (Moz) groups, tert-butyloxycarbonyl (BOC) groups, 9-fluorenylmethyloxycarbonyl (FMOC) groups, benzoyl (Bz) groups, benzyl (Bn) groups, carbamate groups, and p-methoxybenzyl (PMB) groups. In certain embodiments, R represents an amine protecting group compatible with solid phase peptide synthesis, such as a 9-fluorenylmethyloxycarbonyl (FMOC) group or a tert-butyloxycarbonyl (BOC) group.

The composition can be, for example, a solution of the isotopically labeled compound in a solvent. Non-limiting examples of solvents include aliphatic solvents (e.g., pentane, hexanes, cyclohexane); aromatic and/or alkylated aromatic solvents such as benzene, toluene, xylene; hydrocarbon solvents; dichloromethane, chloroform, alcohols (e.g., methanol, ethanol, isopropanol); esters (e.g., ethyl acetate); ketones (e.g., acetone); diethyl ether; dioxane; glycol ethers and glycol ether esters; tetrahydrofuran, dimethylformamide; acetonitrile; dimethyl sulfoxide; water, saline, aqueous buffers (e.g., PBS buffer), and combinations thereof. In certain examples, the composition can comprise an aqueous solution of the compound.

In some embodiments, the isotopically labeled compound can comprise at least 0.5% by weight (e.g., at least 1% by weight, at least 1.5% by weight, at least 2% by weight, at least 2.5% by weight, at least 3% by weight, at least 3.5% by weight, at least 4% by weight, at least 4.5% by weight, or at least 1% by weight of the composition.

The isotopically labeled compounds described above can be prepared using methods known in the art. Representative methodologies for the preparation of certain active agents are described below. The appropriate route for synthesis of a given compound agent can be selected in view of the structure of the compound as a whole as it relates to compatibility of functional groups, protecting group strategies, and the presence of labile bonds. In addition to the synthetic methodologies discussed below, alternative reactions and strategies useful for the preparation of the compounds disclosed herein are known in the art. See, for example, March, "Advanced Organic Chemistry," 5$^{th}$ Edition, 2001, Wiley-Interscience Publication, New York).

Isotopically labeled amino acids, such as $^{13}$C/$^{15}$N-labeled asparagine, are commercially available, and can serve as convenient starting materials for the isotopically labeled compounds described herein. Scheme 1 below illustrates an example method for the preparation of BMAA from asparagine. Compounds having a desired isotopic labeling (e.g., incorporating stable isotopes at particular positions within the compound) can be prepared by selecting reagents that include stable isotope labels at the appropriate positions with their framework (e.g., $^{13}$C/$^{15}$N-labeled asparagine).

Scheme 1. Example method for the preparation of BMAA.

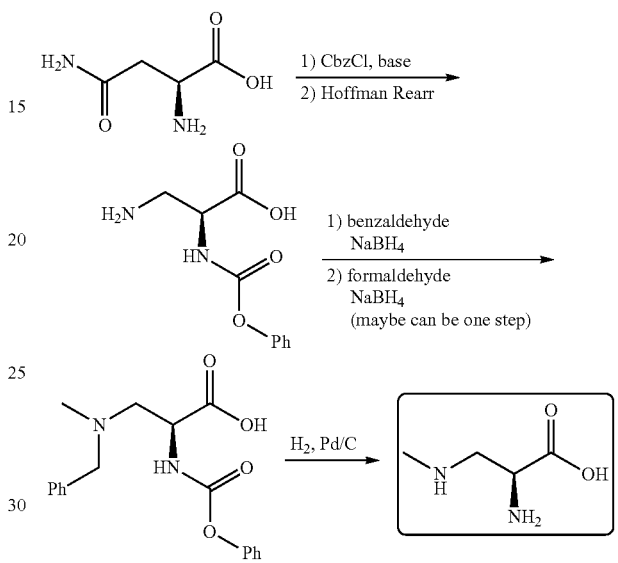

Also provided are compositions that include one or more isotopically labeled polypeptides. For example, compositions comprising a polypeptide that includes one or more isotopically labeled β-N-methylamino-L-alanine (BMAA) residues are provided herein. The isotopically labeled polypeptide can comprise at least 0.5% by weight of the composition. Each of the one or more isotopically labeled BMAA residues can be isotopically labeled with one or more (e.g., two or more) stable isotopes. For example, each of the one or more isotopically labeled BMAA residues can be defined by the formula below

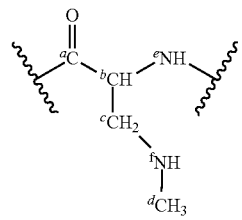

where the $^{13}$C isotopic enrichment factor for $^dC$ is at least 25; and the $^{15}$N isotopic enrichment factor for $^fN$ is at least 100.

In some embodiments, the $^{13}$C isotopic enrichment factor for $^dC$ is at least 25 (27.5% $^{13}$C incorporation at each position), at least 30 (33% $^{13}$C incorporation at each position), at least 35 (38.5% $^{13}$C incorporation at each position), at least 40 (44% $^{13}$C incorporation at each position), at least 45 (49.5% $^{13}$C incorporation at each position), at least 50 (55% $^{13}$C incorporation at each position), at least 55 (60.5% $^{13}$C incorporation at each position), at least 60 (66% $^{13}$C incorporation at each position), at least 65 (71.5% $^{13}C$ incorporation at each position), at least 70 (77% $^{13}C$ incorporation at each position), at least 75 (82.5% $^{13}C$ incorporation at each position), at least 80 (88% $^{13}C$ incorporation at each position), at least 85 (93.5% $^{13}C$ incorporation at each position), or at least 90 (99% $^{13}C$ incorporation at each position).

In some embodiments, the $^{15}N$ isotopic enrichment factor for $^{f}N$ is at least 100 (37% $^{15}N$ incorporation at each position), at least 110 (40.7% $^{15}N$ incorporation at each position), at least 120 (44.4% $^{15}N$ incorporation at each position), at least 130 (48.1% $^{15}N$ incorporation at each position), at least 140 (51.8% $^{15}N$ incorporation at each position), at least 150 (55.5% $^{15}N$ incorporation at each position), at least 160 (59.2% $^{15}N$ incorporation at each position), at least 170 (62.9% $^{15}N$ incorporation at each position), at least 180 (66.6% $^{15}N$ incorporation at each position), at least 190 (70.3% $^{15}N$ incorporation at each position), at least 200 (74% $^{15}N$ incorporation at each position), at least 210 (77.7% $^{15}N$ incorporation at each position), at least 220 (81.4% $^{15}N$ incorporation at each position), at least 230 (85.1% $^{15}N$ incorporation at each position), at least 240 (88.8% $^{15}N$ incorporation at each position), at least 250 (92.5% $^{15}N$ incorporation at each position), at least 260 (96.2% $^{15}N$ incorporation at each position), or at least 265 (98.05% $^{15}N$ incorporation at each position).

Optionally, $^{a}C$, $^{b}C$, and/or $^{c}C$ can also be labeled with a stable isotope. In some cases, the $^{13}C$ isotopic enrichment factor for $^{a}C$, $^{b}C$, and $^{c}C$ can be at least 25 (27.5% $^{13}C$ incorporation at each position), at least 30 (33% $^{13}C$ incorporation at each position), at least 35 (38.5% $^{13}C$ incorporation at each position), at least 40 (44% $^{13}C$ incorporation at each position), at least 45 (49.5% $^{13}C$ incorporation at each position), at least 50 (55% $^{13}C$ incorporation at each position), at least 55 (60.5% $^{13}C$ incorporation at each position), at least 60 (66% $^{13}C$ incorporation at each position), at least 65 (71.5% $^{13}C$ incorporation at each position), at least 70 (77% $^{13}C$ incorporation at each position), at least 75 (82.5% $^{13}C$ incorporation at each position), at least 80 (88% $^{13}C$ incorporation at each position), at least 85 (93.5% $^{13}C$ incorporation at each position), or at least 90 (99% $^{13}C$ incorporation at each position).

Optionally, $^{e}N$ can also be labeled with a stable isotope. In some cases, the $^{15}N$ isotopic enrichment factor for $^{e}N$ is at least 100 (37% $^{15}N$ incorporation at each position), at least 110 (40.7% $^{15}N$ incorporation at each position), at least 120 (44.4% $^{15}N$ incorporation at each position), at least 130 (48.1% $^{15}N$ incorporation at each position), at least 140 (51.8% $^{15}N$ incorporation at each position), at least 150 (55.5% $^{15}N$ incorporation at each position), at least 160 (59.2% $^{15}N$ incorporation at each position), at least 170 (62.9% $^{15}N$ incorporation at each position), at least 180 (66.6% $^{15}N$ incorporation at each position), at least 190 (70.3% $^{15}N$ incorporation at each position), at least 200 (74% $^{15}N$ incorporation at each position), at least 210 (77.7% $^{15}N$ incorporation at each position), at least 220 (81.4% $^{15}N$ incorporation at each position), at least 230 (85.1% $^{15}N$ incorporation at each position), at least 240 (88.8% $^{15}N$ incorporation at each position), at least 250 (92.5% $^{15}N$ incorporation at each position), at least 260 (96.2% $^{15}N$ incorporation at each position), or at least 265 (98.05% $^{15}N$ incorporation at each position).

In some embodiments, the polypeptide can include a single isotopically labeled BMAA residue. In other embodiments, the polypeptide can include two or more isotopically labeled BMAA residues (e.g., three or more isotopically labeled BMAA residues, four or more isotopically labeled BMAA residues, five or more isotopically labeled BMAA residues, or ten or more isotopically labeled BMAA residues).

In some embodiments, the polypeptide can be defined by the formula below where m is an integer from 0 to 300 and n is an integer from 0 to 300; the $^{13}C$ isotopic enrichment factor for $^{d}C$ is at least 25; the $^{15}N$ isotopic enrichment factor for $^{f}N$ is at least 100; and independently for each occurrence in the polypeptide, $R_1$ is H and $R_2$ is selected from one of the following or $R_1$ and $R_2$, together with the atoms to which they are attached, form a five-membered heterocycle defined by the structure below

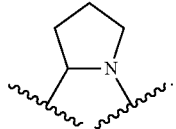

In some embodiments, the polypeptide can be defined by the formula below

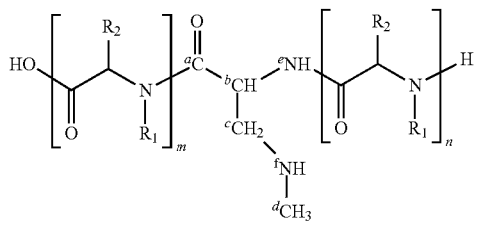

where m is an integer from 0 to 300 and n is an integer from 0 to 300, with the proviso that at least one of m and n is not 0; the $^{13}C$ isotopic enrichment factor for $^dC$ is at least 25; the $^{15}N$ isotopic enrichment factor for $^fN$ is at least 100; and independently for each occurrence in the polypeptide, $R_1$ is H and $R_2$ is selected from one of the following

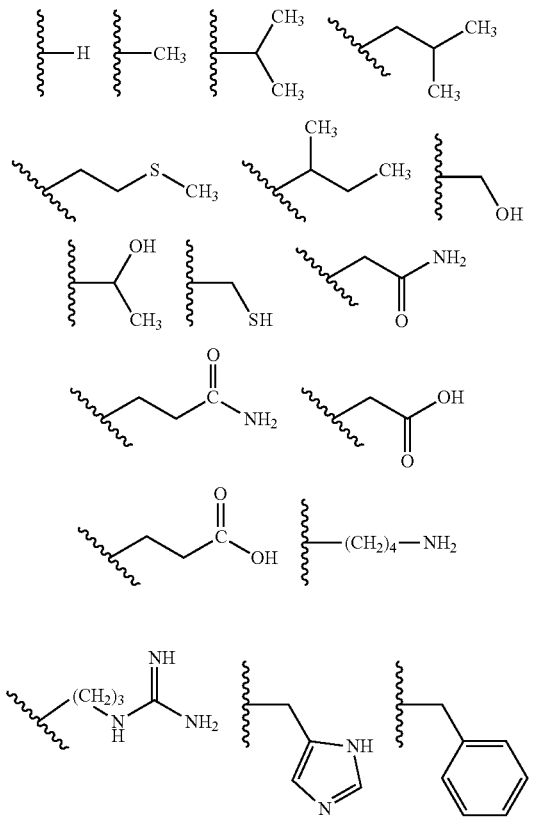

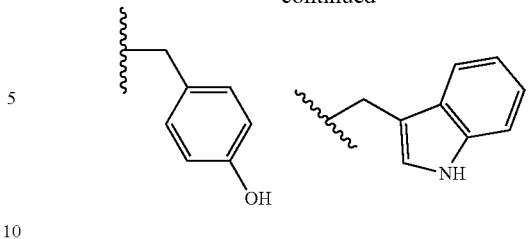

or $R_1$ and $R_2$, together with the atoms to which they are attached, form a five-membered heterocycle defined by the structure below

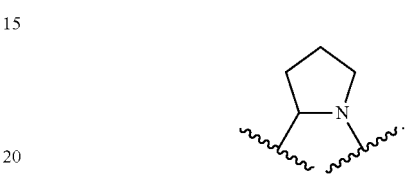

In some embodiments, the $^{13}C$ isotopic enrichment factor for $^dC$ is at least 25 (27.5% $^{13}C$ incorporation at each position), at least 30 (33% $^{13}C$ incorporation at each position), at least 35 (38.5% $^{13}C$ incorporation at each position), at least 40 (44% $^{13}C$ incorporation at each position), at least 45 (49.5% $^{13}C$ incorporation at each position), at least 50 (55% $^{13}C$ incorporation at each position), at least 55 (60.5% $^{13}C$ incorporation at each position), at least 60 (66% $^{13}C$ incorporation at each position), at least 65 (71.5% $^{13}C$ incorporation at each position), at least 70 (77% $^{13}C$ incorporation at each position), at least 75 (82.5% $^{13}C$ incorporation at each position), at least 80 (88% $^{13}C$ incorporation at each position), at least 85 (93.5% $^{13}C$ incorporation at each position), or at least 90 (99% $^{13}C$ incorporation at each position).

In some embodiments, the $^{15}N$ isotopic enrichment factor for $^fN$ is at least 100 (37% $^{15}N$ incorporation at each position), at least 110 (40.7% $^{15}N$ incorporation at each position), at least 120 (44.4% $^{15}N$ incorporation at each position), at least 130 (48.1% $^{15}N$ incorporation at each position), at least 140 (51.8% $^{15}N$ incorporation at each position), at least 150 (55.5% $^{15}N$ incorporation at each position), at least 160 (59.2% $^{15}N$ incorporation at each position), at least 170 (62.9% $^{15}N$ incorporation at each position), at least 180 (66.6% $^{15}N$ incorporation at each position), at least 190 (70.3% $^{15}N$ incorporation at each position), at least 200 (74% $^{15}N$ incorporation at each position), at least 210 (77.7% $^{15}N$ incorporation at each position), at least 220 (81.4% $^{15}N$ incorporation at each position), at least 230 (85.1% $^{15}N$ incorporation at each position), at least 240 (88.8% $^{15}N$ incorporation at each position), at least 250 (92.5% $^{15}N$ incorporation at each position), at least 260 (96.2% $^{15}N$ incorporation at each position), or at least 265 (98.05% $^{15}N$ incorporation at each position).

Optionally, $^aC$, $^bC$, and/or $^cC$ can also be labeled with a stable isotope. In some cases, the $^{13}C$ isotopic enrichment factor for $^aC$, $^bC$, and $^cC$ can be at least 25 (27.5% $^{13}C$ incorporation at each position), at least 30 (33% $^{13}C$ incorporation at each position), at least 35 (38.5% $^{13}C$ incorporation at each position), at least 40 (44% $^{13}C$ incorporation at each position), at least 45 (49.5% $^{13}C$ incorporation at each position), at least 50 (55% $^{13}C$ incorporation at each position), at least 55 (60.5% $^{13}C$ incorporation at each position), at least 60 (66% $^{13}C$ incorporation at each position), at least 65 (71.5% $^{13}$C incorporation at each position), at least 70 (77% $^{13}$C incorporation at each position), at least 75 (82.5% $^{13}$C incorporation at each position), at least 80 (88% $^{13}$C incorporation at each position), at least 85 (93.5% $^{13}$C incorporation at each position), or at least 90 (99% $^{13}$C incorporation at each position).

Optionally, $^e$N can also be labeled with a stable isotope. In some cases, the $^{15}$N isotopic enrichment factor for $^e$N is at least 100 (37% $^{15}$N incorporation at each position), at least 110 (40.7% $^{15}$N incorporation at each position), at least 120 (44.4% $^{15}$N incorporation at each position), at least 130 (48.1% $^{15}$N incorporation at each position), at least 140 (51.8% $^{15}$N incorporation at each position), at least 150 (55.5% $^{15}$N incorporation at each position), at least 160 (59.2% $^{15}$N incorporation at each position), at least 170 (62.9% $^{15}$N incorporation at each position), at least 180 (66.6% $^{15}$N incorporation at each position), at least 190 (70.3% $^{15}$N incorporation at each position), at least 200 (74% $^{15}$N incorporation at each position), at least 210 (77.7% $^{15}$N incorporation at each position), at least 220 (81.4% $^{15}$N incorporation at each position), at least 230 (85.1% $^{15}$N incorporation at each position), at least 240 (88.8% $^{15}$N incorporation at each position), at least 250 (92.5% $^{15}$N incorporation at each position), at least 260 (96.2% $^{15}$N incorporation at each position), or at least 265 (98.05% $^{15}$N incorporation at each position).

In some embodiments, m can be at least 1 (e.g., at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, or at least 290). In some embodiments, m can be 300 or less (e.g., 290 or less, 280 or less, 270 or less, 260 or less, 250 or less, 240 or less, 230 or less, 220 or less, 210 or less, 200 or less, 190 or less, 180 or less, 170 or less, 160 or less, 150 or less, 140 or less, 130 or less, 120 or less, 110 or less, 100 or less, 90 or less, 80 or less, 70 or less, 60 or less, 50 or less, 40 or less, 30 or less, 20 or less, 10 or less, or 5 or less). m can be an integer ranging from any of the minimum values described above to any of the maximum values described above. For example, in some embodiments, m can be an integer from 1 to 300 (e.g., from 1 to 150, from 1 to 100, from 1 to 50, from 1 to 30, or from 1 to 10).

In some embodiments, n can be at least 1 (e.g., at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, or at least 290). In some embodiments, n can be 300 or less (e.g., 290 or less, 280 or less, 270 or less, 260 or less, 250 or less, 240 or less, 230 or less, 220 or less, 210 or less, 200 or less, 190 or less, 180 or less, 170 or less, 160 or less, 150 or less, 140 or less, 130 or less, 120 or less, 110 or less, 100 or less, 90 or less, 80 or less, 70 or less, 60 or less, 50 or less, 40 or less, 30 or less, 20 or less, 10 or less, or 5 or less). n can be an integer ranging from any of the minimum values described above to any of the maximum values described above. For example, in some embodiments, n can be an integer from 1 to 300 (e.g., from 1 to 150, from 1 to 100, from 1 to 50, from 1 to 30, or from 1 to 10).

In some embodiments, the sum of m and n can be at least 1 (e.g., at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, at least 390, at least 400, at least 410, at least 420, at least 430, at least 440, at least 450, at least 460, at least 470, at least 480, at least 490, at least 500, at least 510, at least 520, at least 530, at least 540, at least 550, at least 560, at least 570, at least 580, or at least 590). In some embodiments, the sum of m and n can be 600 or less (e.g., 590 or less, 580 or less, 570 or less, 560 or less, 550 or less, 540 or less, 530 or less, 520 or less, 510 or less, 500 or less, 490 or less, 480 or less, 470 or less, 460 or less, 450 or less, 440 or less, 430 or less, 420 or less, 410 or less, 400 or less, 390 or less, 380 or less, 370 or less, 360 or less, 350 or less, 340 or less, 330 or less, 320 or less, 310 or less, 300 or less, 290 or less, 280 or less, 270 or less, 260 or less, 250 or less, 240 or less, 230 or less, 220 or less, 210 or less, 200 or less, 190 or less, 180 or less, 170 or less, 160 or less, 150 or less, 140 or less, 130 or less, 120 or less, 110 or less, 100 or less, 90 or less, 80 or less, 70 or less, 60 or less, 50 or less, 40 or less, 30 or less, 20 or less, 10 or less, or 5 or less). The sum of m and n can so range from any of the minimum values described above to any of the maximum values described above. For example, in some embodiments, the sum of m and n can be from 1 to 600 (e.g., from 1 to 300, from 1 to 150, from 1 to 100, from 1 to 50, from 1 to 30, from 1 to 10, from 5 to 300, from 5 to 150, from 5 to 100, from 5 to 50, from 5 to 30, or from 5 to 10).

The composition can be, for example, a solution of the isotopically labeled peptide in a solvent. Non-limiting examples of solvents include alcohols (e.g., methanol, ethanol, isopropanol); esters (e.g., ethyl acetate); ketones (e.g., acetone); diethyl ether; dioxane; glycol ethers and glycol ether esters; tetrahydrofuran, dimethylformamide; acetonitrile; dimethyl sulfoxide; water, saline, aqueous buffers (e.g., PBS buffer), and combinations thereof. In certain examples, the composition can comprise an aqueous solution of the peptide.

In some embodiments, the isotopically labeled peptide can comprise at least 0.5% by weight (e.g., at least 1% by weight, at least 1.5% by weight, at least 2% by weight, at least 2.5% by weight, at least 3% by weight, at least 3.5% by weight, at least 4% by weight, at least 4.5% by weight, or at least 1% by weight of the composition.

Also provided are compositions comprising an isotopically labeled polypeptide that includes one or more β-N-methylamino-L-alanine (BMAA) residues (e.g., one or more BMAA residues that are not isotopically labeled) and one or more additional amino acid residues that are labeled with one or more stable isotopes ($^{13}$C, $^{15}$N, and/or $^{18}$O). In some embodiments, each residue labeled with one or more stable isotopes in the polypeptide includes at least two (e.g., at least four, at least five, at least six, or more) stable isotopes. For example, at least two (e.g., at least four, at least five, at least six, or more) of the carbon, nitrogen, and/or oxygen atoms in the residue can be isotopically labeled with a stable isotope. In some cases, at least two (e.g., at least four, at least five, at least six, or more) of the carbon and/or nitrogen atoms in the residue can be isotopically labeled with a stable isotope. The isotopically labeled polypeptide can comprise at least 0.5% by weight of the composition.

In some embodiments, the polypeptide can include a single isotopically labeled residue. In other embodiments, the polypeptide can include two or more isotopically labeled residues (e.g., three or more isotopically labeled residues, four or more isotopically labeled residues, five or more isotopically labeled residues, or ten or more isotopically labeled residues). In some embodiments, the polypeptide can include a single BMAA residue. In other embodiments, the polypeptide can include two or more BMAA residues (e.g., three or more BMAA residues, four or more BMAA residues, five or more BMAA residues, or ten or more BMAA residues).

In certain embodiments, the isotopically labeled polypeptide can be a peptide that includes one or more BMAA residues and a terminal amino acid residue (e.g., a terminal arginine residue) labeled with one or more stable isotopes ($^{13}C$, $^{15}N$, and/or $^{18}O$).

The composition can be, for example, a solution of the isotopically labeled peptide in a solvent. Non-limiting examples of solvents include alcohols (e.g., methanol, ethanol, isopropanol); esters (e.g., ethyl acetate); ketones (e.g., acetone); diethyl ether; dioxane; glycol ethers and glycol ether esters; tetrahydrofuran; dimethylformamide; acetonitrile; dimethyl sulfoxide; water, saline, aqueous buffers (e.g., PBS buffer), and combinations thereof. In certain examples, the composition can comprise an aqueous solution of the peptide.

In some embodiments, the isotopically labeled peptide can comprise at least 0.5% by weight (e.g., at least 1% by weight, at least 1.5% by weight, at least 2% by weight, at least 2.5% by weight, at least 3% by weight, at least 3.5% by weight, at least 4% by weight, at least 4.5% by weight, or at least 1% by weight of the composition.

The peptides described above can be above can be prepared using a variety of methods known in the art. For example, peptides can be prepared using the isotopically labeled compounds described herein via solid phase peptide synthesis. The proteins and peptides described above can also be prepared by chemical derivatization of one or more residues within the protein and peptide. For example, a protein or peptide having a isotopically labeled β-N-methylamino-L-alanine (BMAA) residue can be prepared from a protein or peptide that includes a phosphoserine residue. The protein or peptide can be reacted to convert the phosphoserine residue to an α,β-unsaturated amino acid residue. Once activated, the α,β-unsaturated amino acid residue can be reacted with methylamine (e.g., methylamine that is isotopically enriched with one or more stable isotopes), which undergoes a Michael-type addition to afford an isotopically labeled BMAA residue. This can involve, for example, reaction of the protein or peptide with methylamine-HCl (e.g., 1.0 M $^{13}C/^{15}N$-labeled methylamine) and Ba(OH)$_2$ (e.g., 0.1 M Ba(OH)$_2$) in water/DMSO/EtOH (2:2:1) at basic pH (pH 12.5) and elevated temperature (e.g., 37° C.). Once complete, the reaction can be quenched with acid (e.g., acetic acid).

Full length natural or stable isotope labeled proteins comprising stable isotope labeled BMAA residues (e.g., incorporated at one or more specific sites within the protein) can be prepared by first preparing a phosphoserine-containing protein using an amber stop codon and a tRNA synthetase engineered to incorporate phosphoserine within the desired protein. See, for example, Rogerson, D. T. et al. "Efficient genetic encoding of phosphoserine and its non-hydrolyzable analog." *Nat. Chem. Biol.*, 2015, 7: 496-503. The protein can then be isolated, and the phosphoserine can be chemically converted into BMAA using the strategy described above.

Methods

The compounds, peptides, proteins, and compositions described herein can be used detect and/or quantify BMAA in a sample (e.g., an environmental sample or a biological sample), to accurately monitor BMAA exposure, to direct therapies, and in clinical diagnosis and prognosis. These materials can be utilized in a wide range of analytical pipelines and applications which require stable isotope labeled standards (SIL) for BMAA, protein specific peptides containing BMAA, and target proteins containing BMAA.

For example, the isotopically labeled reagents and compositions described herein can be used in a variety of analytical methods to detect and/or quantify BMAA, such as to detect and/or quantify BMAA in a biological sample such as a protein sample. The isotopically labeled compounds described herein can be used to quantify free BMAA (e.g., quantify free BMAA in an environmental sample or biological sample), quantify total levels of BMAA in a protein sample, and/or to quantify protein-specific BMAA incorporation (e.g., by upstream purification of the protein of interest prior to analysis). The isotopically labeled compounds described herein can also be utilized in a stable isotope labeling by amino acids in cell culture (SILAC) alone or in combination with other stable isotope labeled amino acids. The isotopically labeled compounds described herein provide many analytical advantages over potential alternatives, such as deuterated BMAA, which does not co-elute and can undergo hydrogen-deuterium exchange in-solution or in the gas phase, significantly impacting identification and quantitation.

In some embodiments, methods for quantifying the amount of BMAA in a sample can comprise: (i) analyzing a test sample by mass spectrometry; (ii) spiking the test sample with a defined amount of an isotopically labeled compound defined by the formula below

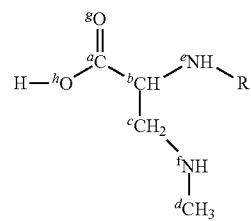

where R represents hydrogen or an amine protecting group, and at least two of $^aC$, $^bC$, $^cC$, $^dC$, $^eN$, $^fN$, $^gO$, and $^hO$ are isotopically labeled with a stable isotope; to provide a BMAA-spiked sample; (iii) analyzing the BMAA-spiked sample by mass spectrometry; and (iv) determining the amount of BMAA in the test sample by isotope dilution analysis. Methods can further comprise preparing the test sample, the BMAA-spiked sample, or a combination thereof for analysis by mass spectrometry. For example, the test sample, the BMAA-spiked sample, or a combination thereof can be prepared for analysis by mass spectrometry by a method comprising chemical reactions with flight enhancers, chemical fragmentation, enzymatic digestion, purification, or a combination thereof. In some embodiments, the isotopically labeled compounds described herein can be used to detect and quantify BMAA obtained from the hydrolytic cleavage of amino acids from a target protein as well as for identification and quantification of BMAA incorporated into proteins at the peptide and protein level utilizing isotope dilution mass spectrometry.

The proteins and peptides described herein can be used as diagnostic markers, to monitor exposure to BMAA, and/or to identify disease relevant and functionally important proteins in which BMAA has been incorporated in specific sequence locations. The proteins and peptides described herein can be utilized in a protein-cleavage-isotope dilution workflow to confirm the primary structure, and to accurately and precisely quantify BMAA incorporated into peptides produced via chemical or enzymatic digestion of specific proteins.

These proteins and peptides can also be employed in separation schemes, followed by intact mass spectrometry or peptide level detection and quantification through chemical or proteolytic digestion. These proteins and peptides can also be used to produce antibodies, aptamers and/or other affinity reagents which can be utilized for other diagnostic tools and applications. These proteins and peptides can also be used in biophysical studies, providing a method for studying the effect of this non-protein amino acid incorporation in proteins.

By way of non-limiting illustration, examples of certain embodiments of the present disclosure are given below.

EXAMPLES

Example 1: Preparation of $^{13}C_3{}^{15}N_2$ β-N-Methylamino-L-Alanine

Preparation of Compound 1.

To a solution of $^{13}C$-$^{15}N$ labeled L-asparagine monohydrate (95.8 mg, 0.614 mmol) in 10% aqueous $Na_2CO_3$ (1.6 mL) was added 1,4-dioxane (0.9 mL) and the mixture was cooled to 0° C. Benzyl chloroformate (130 mg, 0.737 mmol) was then added and the mixture was allowed to warm to rt overnight. The reaction mixture was poured into water (4.0 mL), and the mixture was extracted with diethyl ether (×3). The aqueous layer was then acidified with an aqueous solution of 2N HCl (pH=2), and the white solid was filtered to afford 98.5 mg (59%) of the product: $^1$H NMR (400 MHz, CDCl$_3$) δ 7.37 (m, 5H), 5.10 (m, 2H), 4.25 (bd, 1H, J=132.1 Hz), 2.81 (bd, 1H, J=44.1 Hz), 2.46 (bd, 1H, J=64.6 Hz); ESIMS m/z 273 [M+H]$^+$; HRMS m/z calculated for $^{13}C_4C_8H_{14}{}^{15}N_2O_5$ [M+Na]$^+$ 295.0870, found 295.0867.

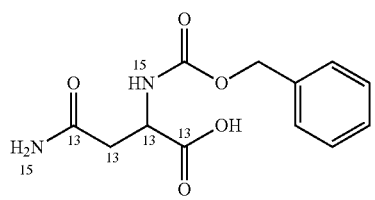

(1)

Preparation of Compound 2.

To a slurry of N$^2$-benzyloxycarbonylasparagine (98.5 mg, 0.362 mmol) in ethyl acetate (0.89 mL), acetonitrile (0.96 mL), and water (0.46 mL) was added iodosobenzene diacetate (0.166 g, 0.507 mmol) at 15° C. and the mixture was stirred for 30 min at 15° C. The reaction mixture was then allowed to warm to rt and stirred until completion (4 h). The mixture was cooled to 5° C., and the product was collected, washed with ethyl acetate, and dried in vacuo to afford 33.9 mg (39%) of the product as a white solid: $^1$H NMR (400 MHz, CDCl$_3$) δ 8.03 (brs, 1H), 7.85 (brs, 2H), 7.40 (s, 5H), 5.07 (s, 2H), 4.30 (bd, 1H, J=139.2 Hz), 3.31 (bd, 1H, J=83.9 Hz), 3.31 (bd, 1H, J=83.9 Hz), 2.95 (bd, 1H, J=87.9 Hz); ESIMS m/z 244 [M+H]$^+$; HRMS m/z calculated for $^{13}C_3C_8H_{14}{}^{15}N_2O_4$ [M+H]$^+$ 244.1068, found 244.1066.

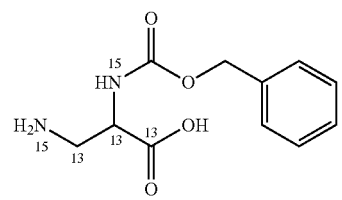

(2)

Preparation of Compound 3.

To a suspension of compound 3 (33.9 mg, 0.139 mmol) in methanol (0.60 mL) was added Et$_3$N (42.3 mg, 0.416 mmol) and benzaldehyde (29.6 mg, 0.278 mmol) at rt, and the mixture was stirred for 30 min. The reaction mixture was cooled to 0° C., followed by the addition of NaBH$_4$ (16.0 mg, 0.416 mmol). The mixture was then stirred for an additional 15 min at 0° C., and concentrated under reduced pressure. The residue was then dissolved in 0.1 M aqueous solution of NaOH, and extracted with diethyl ether (×3). The aqueous layer was then acidified with an aqueous solution of 10% hydrochloric acid, and the resultant white precipitate was filtered to afford 27.2 mg of the product. The white solid was dissolved in methanol (0.27 mL), and a solution of 35% aqueous solution of formaldehyde (18.2 μL, 0.244 mmol) was added. The reaction was stirred for an additional 15 min, and cooled to 0° C. NaBH$_4$ (9.32 mg, 0.244 mmol) was then added, and the mixture was stirred for 15 min. Upon completion, the mixture was concentrated under reduced pressure, and the crude residue was dissolved in water, acidified (pH=6) with a 1 M aqueous solution of HCl, extracted with CHCl$_3$, dried (MgSO$_4$), and concentrated under reduced pressure to afford the crude product. The crude product was triturated with diethyl ether to afford 28.3 mg (100%) of the product as a white solid: $^1$H NMR (400 MHz, CDCl$_3$) δ 7.18 (s, 10H), 6.38 (d, 1H, J=92.5 Hz), 5.09 (d, 1H, J=16.5 Hz), 4.88 (d, 1H, J=15.4 Hz), 4.19 (d, 1H, J=83.9 Hz), 3.58 (d, 1H, J=13.2 Hz), 3.48 (d, 1H, J=16.1 Hz), 3.01 (s, 1H), 2.67 (s, 1H), 2.12 (s, 3H); ESIMS m/z 348 [M+H]$^+$; HRMS m/z calculated for $^{13}C_3C_{16}H_{22}{}^{15}N_2O_4$ [M+H]$^+$ 348.1694, found 348.1690.

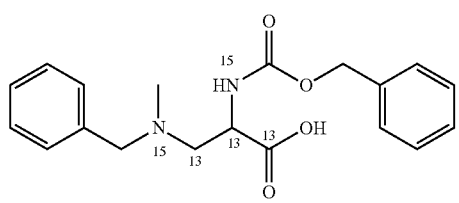

(3)

Preparation of Compound $^{13}C_3{}^{15}N_2$ β-N-Methylamino-L-Alanine.

Figure 11:
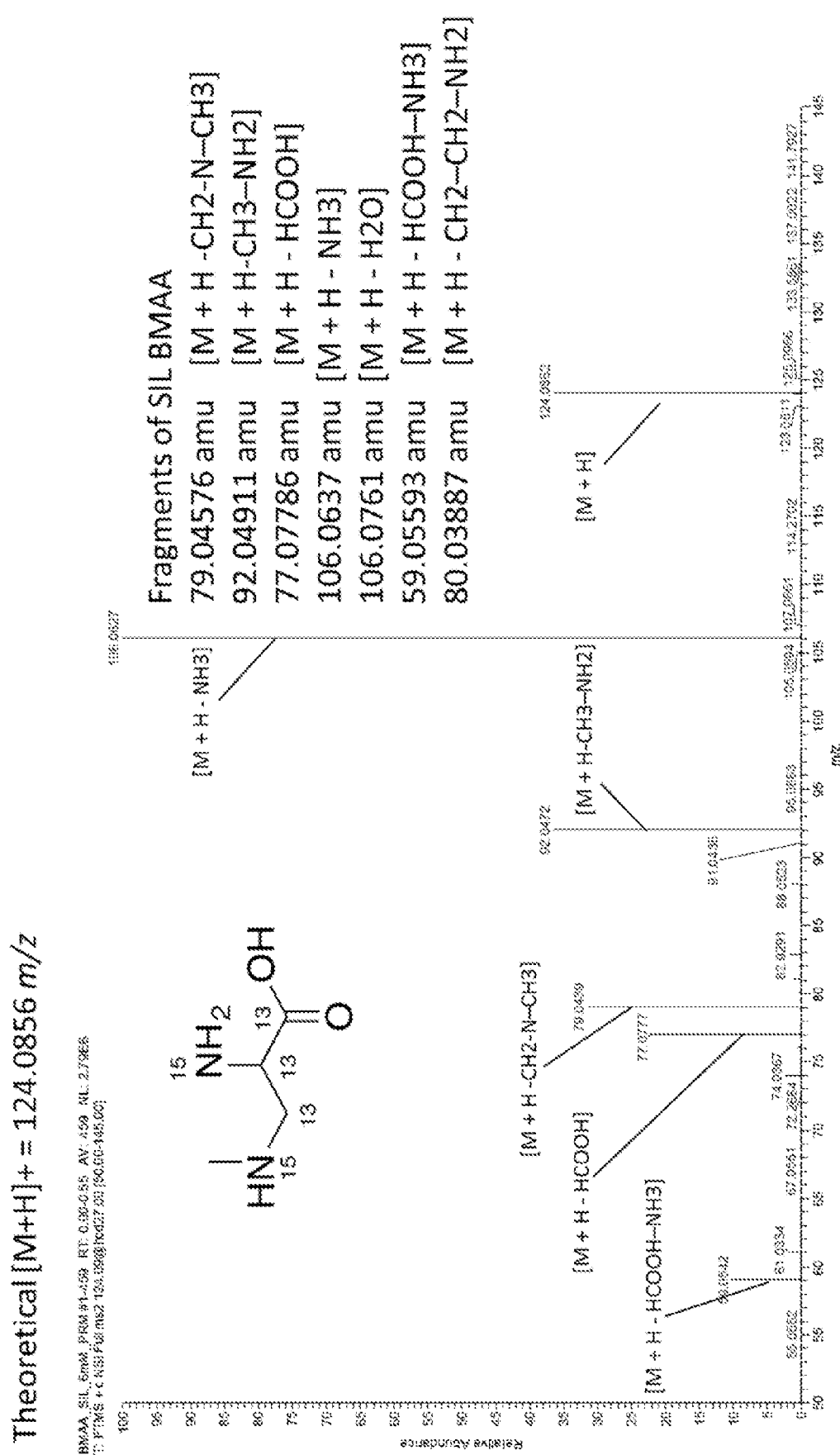
FIG. 11 illustrates the tandem mass spectrum of a BMAA-containing stable isotope-labeled peptide. Fragment ions corresponding to the endogenous peptide with BMAA were found at the expected location, confirming localization of modification.
Figure 13:
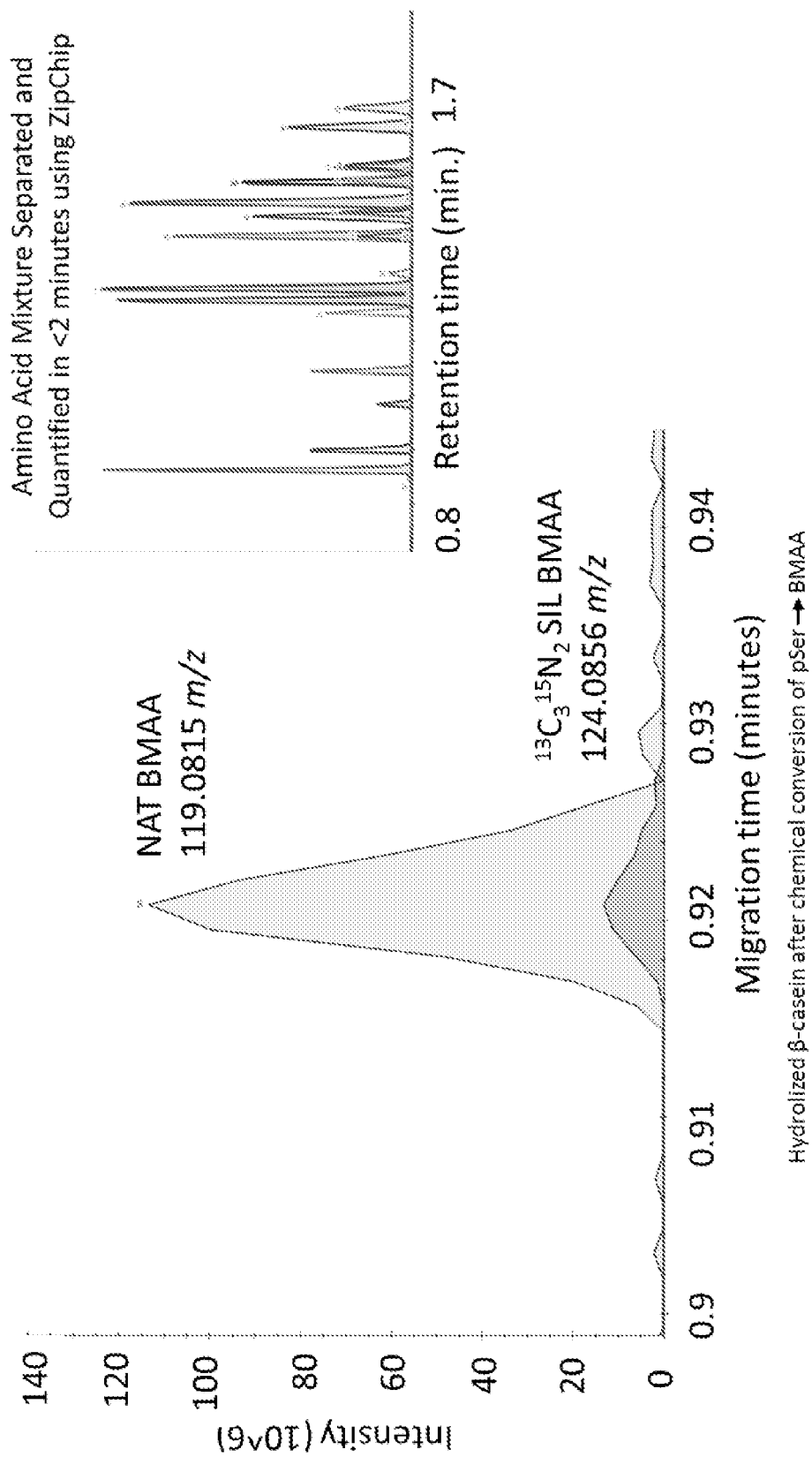
FIG. 13 shows an extracted electropherogram of SIL BMAA and endogenous BMAA from ZipChip CZE-MS of Hydrolyzed b-casein after chemical conversion of phosphoserine to BMAA.

To a degassed solution of compound 3 (28.3 mg, 0.0814 mmol) in methanol (0.8 mL) was added Pd/C (8.66 mg, 0.00813 mmol), and the mixture was further degassed for an additional 5 min. The mixture was then saturated with H$_2$ gas and stirred under a H$_2$ atmosphere overnight. The Pd/C was filtered through Celite®, and washed with methanol. The filtrated was concentrated under reduced pressure and the crude product was triturated with diethyl ether to afford 7.7 mg (77%) of the product as a white solid: ESIMS m/z 146 [M+Na]+; HRMS m/z calculated for $^{13}C_3CH_{10}^{15}N_2O_2$ [M+H]+ 124.0856, found 124.0856. This final product was characterized by MS/MS to confirm the exact structure (FIG. 11).

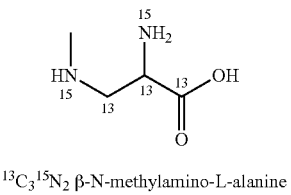

$^{13}C_3^{15}N_2$ β-N-methylamino-L-alanine

A well-characterized, highly phosphorylated protein, Beta-Casein, was utilized as a positive control. The intact protein was reacted with methylamine under the same conditions for peptide synthesis, converting phosphoserines to BMAA. Purified SOD1 from 3 patients with sporadic ALS and 3 healthy controls were washed on a 10 kDa FASP filter (Millipore) and concentrated to 50 μL. 20 μg of protein was hydrolyzed using 50 μL of 6N HCl and incubating at 110° C. for 18 hours. 5 μL of 60.9 mM SIL BMAA was spiked into the samples post-hydrolysis. Samples were then dried and resuspended in 100 μL of 0.001% Zwittergent 3-16. Direct infusion ESI MS/MS of SIL BMAA confirmed the location of isotope incorporation A ZipChip (908 Devices) capillary electrophoresis was utilized to separate BMAA prior to electrospray ionization mass spectrometry. Accurate intact mass and migration time of the SIL reagent was used to identify BMAA.

Figure 2B:
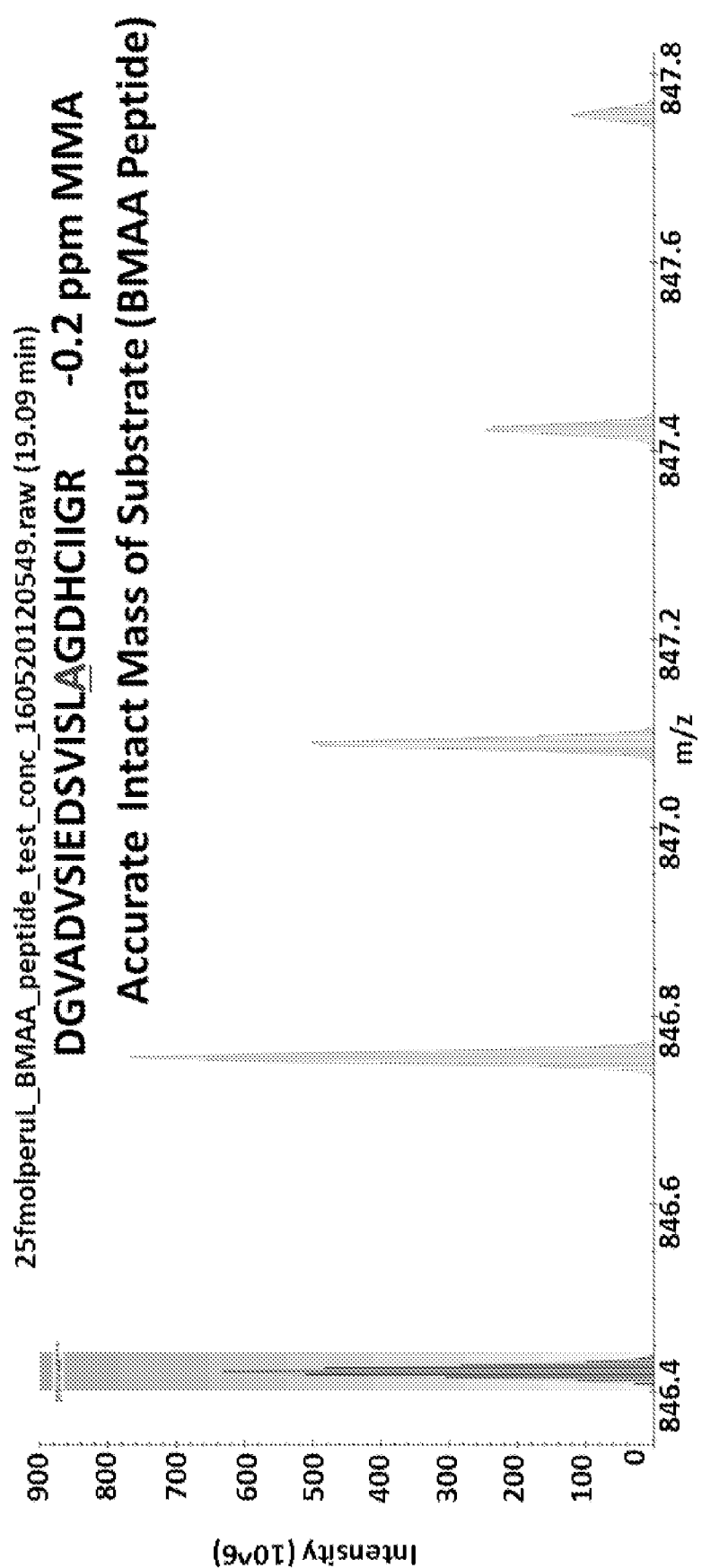
Figure 3:
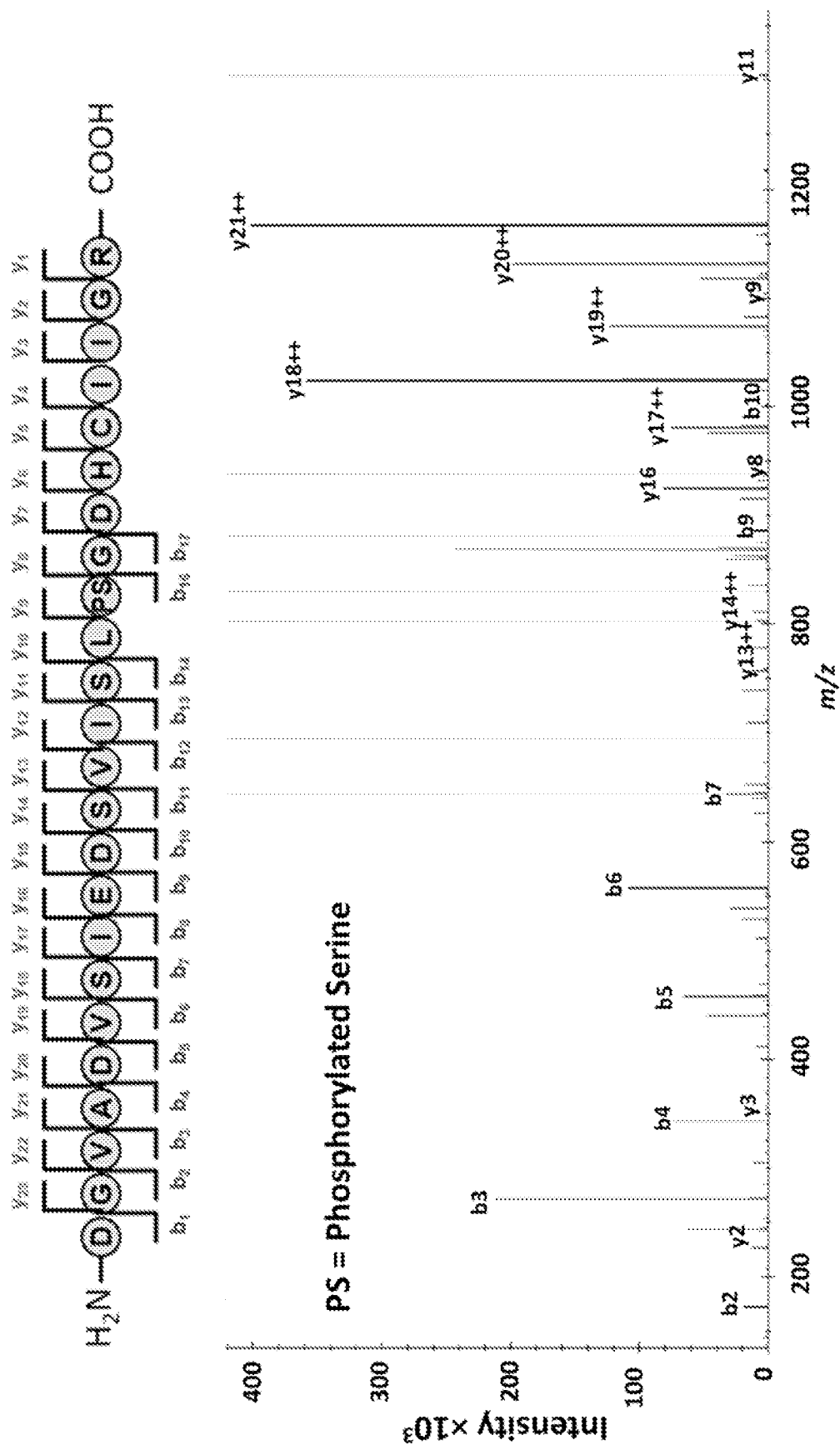
FIG. 3 illustrates the tandem mass spectrum of the phosphorylated serine-containing stable isotope-labeled peptide.
Figure 4:
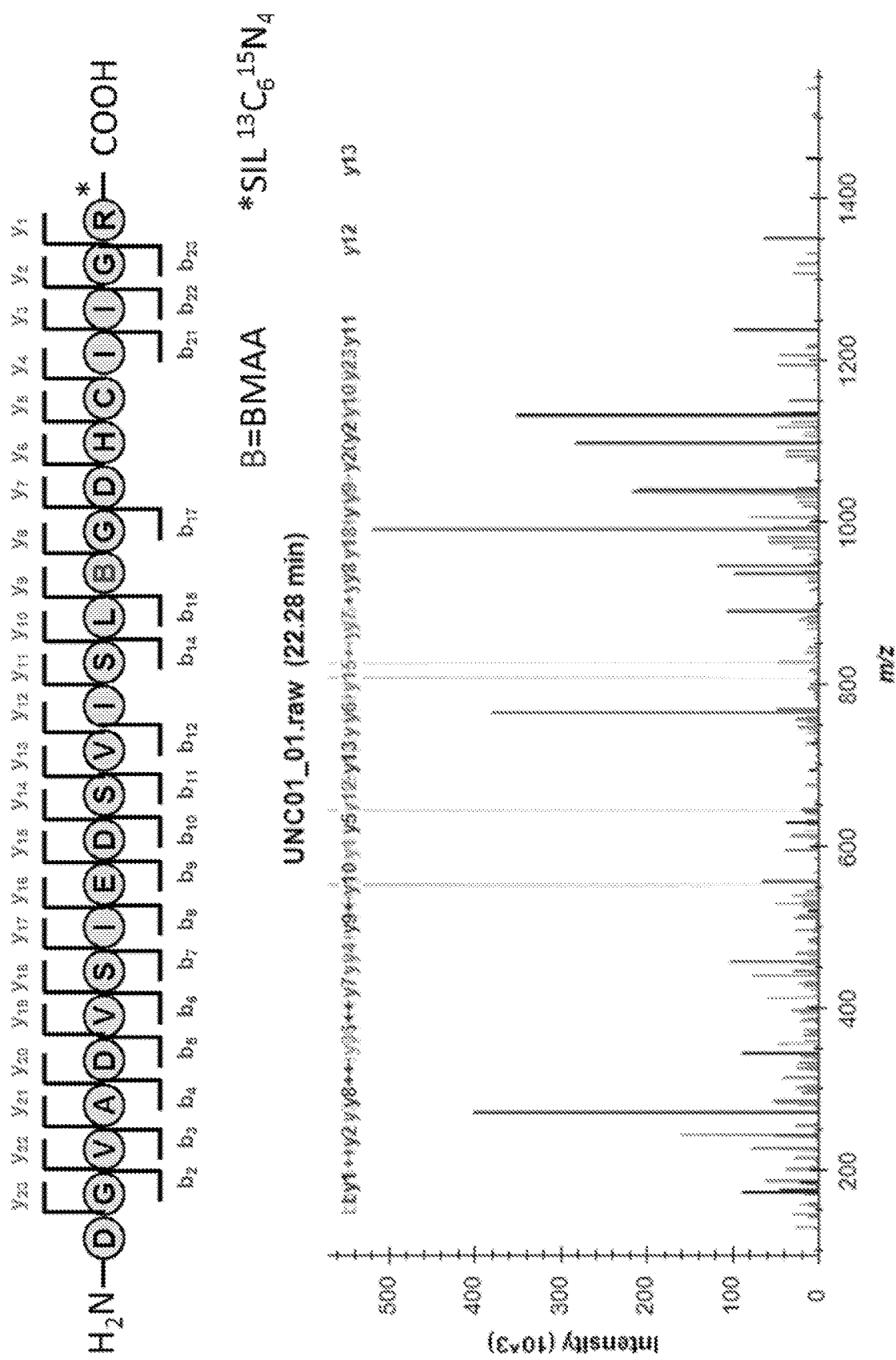
FIG. 4 illustrates the tandem mass spectrum of a BMAA-containing stable isotope-labeled peptide, confirming localization of modification.
Figure 5:
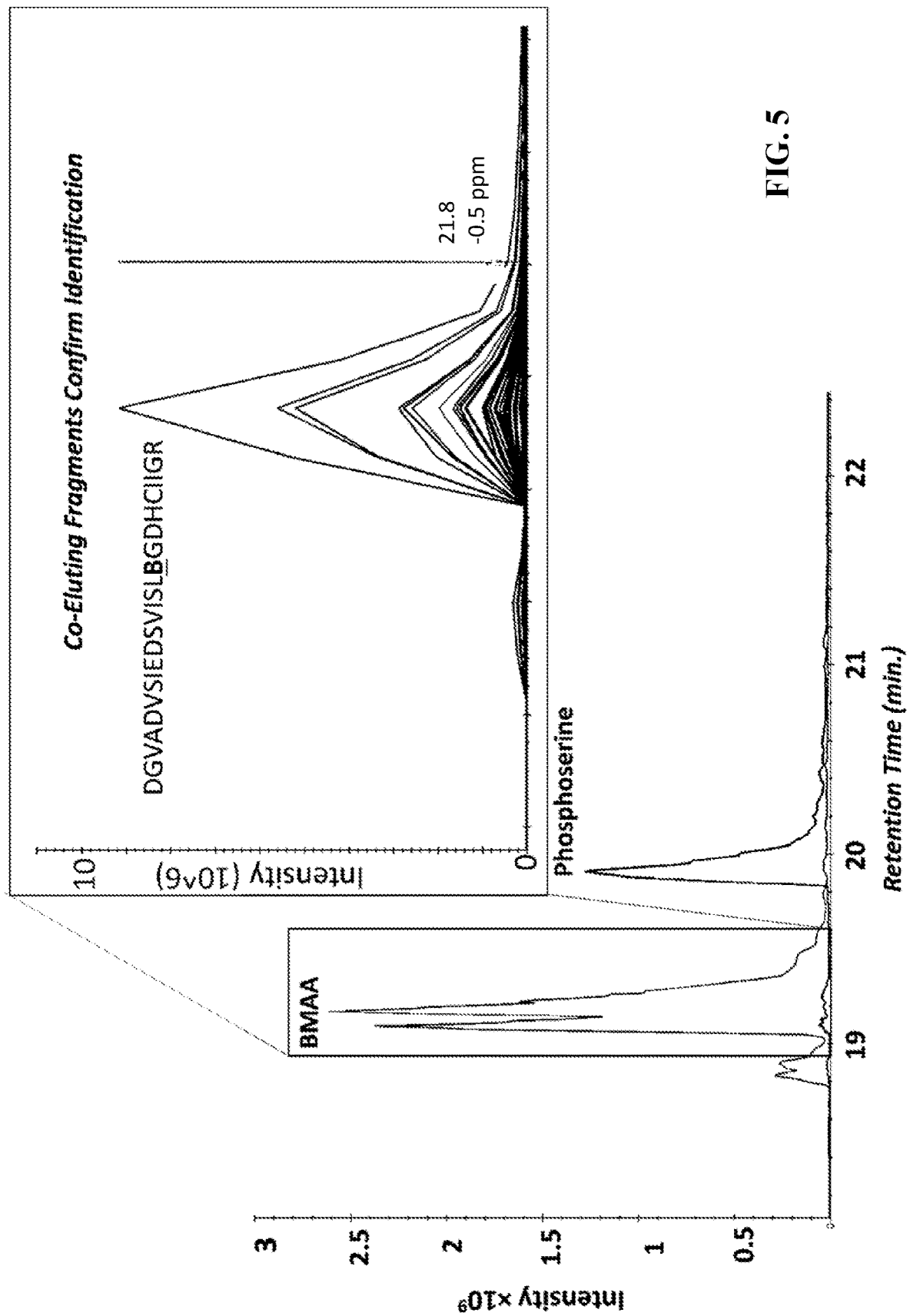
FIG. 5 demonstrates that co-eluting fragments confirm identity of the BMAA-containing peptide BMAA- and phosphoserine-containing peptides have distinct retention times. The BMAA-containing peptide appears to have two peaks which suggests L and D isomers of the BMAA peptide have been produced.

The peptide sequence DGVADVSIEDSVISL$\underline{S}$GDH$\underline{C}$IIG$\underline{R}$ with highlighted (bold and underlined) Serine phosphorylated, carbamidomethylated Cysteine and $^{13}C_6^{15}N_4$ isotopically labeled Arginine was obtained from New England Peptide. This sequence was validated by accurate intact mass (FIG. 2) and MS/MS (FIG. 3) which allowed for site specific confirmation of phosphorylation. A solution of water, DMSO, EtOH solution in 2:2:1 mixture containing 0.1M Barium Hydroxide and 1M Methylamine pH 12.5 was used for derivatization of the SIL peptide. 5 μL (5 μg) of peptide was added to 20 μL of derivatization solution and incubated at 37° C. for two hours. The reaction was quenched with 2 μL of Acetic Acid. See FIG. 1 for synthesis reference. The formation of BMAA at the phosphorylated Serine residue was confirmed by accurate intact mass (FIG. 2) and MS/MS (FIG. 4). Further, the R.T of the BMAA peptide was distinctly different from that of the phosphorylated peptide (FIG. 5), along with co-elution of fragment ions to confirm the identity of this species. The conserved relative abundance of the fragments belonging to the SIL BMAA peptide act as a standard for further confirmation.

Each sample was diluted 2-fold in a denaturing solution of 100 mM DTT (15.43 mg/mL) and 8 M urea. Then the samples were incubated at 56° C. for 30 minutes. After incubation enough alkylation solution, made from 1 M iodoacetamide (184.96 mg/mL) and 8 M urea, was added to give each sample a final iodoacetamide concentration of 200 mM. Then the samples were incubated at 37° C. for an hour. The appropriate amount for each sample was pipetted into an Amicon Ultra-0.1 MWCO-filter unit (10 kDa, Millipore). These were centrifuged for 15 minutes at 14,000×g and 20° C.; when finished the eluent was discarded. The remaining volume was diluted with 400 uL of a digestion buffer made of 2 M urea (102.12 mg/mL) and 10 mM CaCl_2 (1.11 mg/mL). The samples were centrifuged again for 15 minutes at 14,000×g and 20° C. This was repeated two more times, making sure to discard the eluent after each run. After the final centrifugation the collection tubes were changed and 45 uL of modified porcine trypsin reconstituted in 2 M urea and 10 mM CaCl_2 was added and the samples were incubated at 37° C. overnight. Then the samples were quenched with 50 uL of 1% formic acid (v/v) and 0.001% Zwittergent 3-16 and centrifuged for 15 minutes at 14,000×g and 20° C. 400 uL of quench buffer was added to the retained volume and centrifuged again for 15 minutes at 14,000×g and 20° C. Samples were frozen at −80° C. and lyophilized in a speedvac. Immediately prior to analysis samples were reconstituted in 90 uL of Zwittergent 3-16. A BMAA peptide dry aliquot of 5 ug was resuspended in 500 uL of Zwittergent. A 45 uL aliquot of the protein digest was then spiked with 5 uL of BMAA peptide standard for LC-MS analysis.

LC-MS/MS by parallel reaction monitoring was used to isolate, fragment and perform accurate mass measurements of our target endogenous BMAA peptide and SIL BMAA peptides. Direct inject column configuration on a Thermo Easy nano-LC 1000 system coupled to a QExactive High Field mass spectrometer was used. Analytical columns were made using 75 um×15 cm PicoFrit columns (New Objective, Woburn, Mass.) which were self-packed with Kinetex C18 26-um particles (phenomenex, Torrance, Calif., USA). The samples were loaded with a 10 uL injection volume of mobile phase A (98% water, 2% acetonitrile, and 0.2% formic acid) with a max pressure of 500 Bar. A 45 minute run from 2% to 30% mobile phase B (98% acetonitrile, 2% water, and 0.2% formic acid) was performed at a flow rate of 300 nL/min. The analysis had the following parameters: a spray voltage of +1750.00, capillary temperature of 325° C., a S-lens RF level of 65.00, a MS/MS resolving power of 15,000, a 1e6 AGC target, a 1,000 ms fill time, a 2.5 m/z isolation window with an isolation offset of 1.0 m/z, a fixed first mass of 125.0 m/z, and a 20, 30 stepped normalized collision energy. There was an inclusion list containing 846.4228 m/z and 843.0867 m/z.

Figure 7:
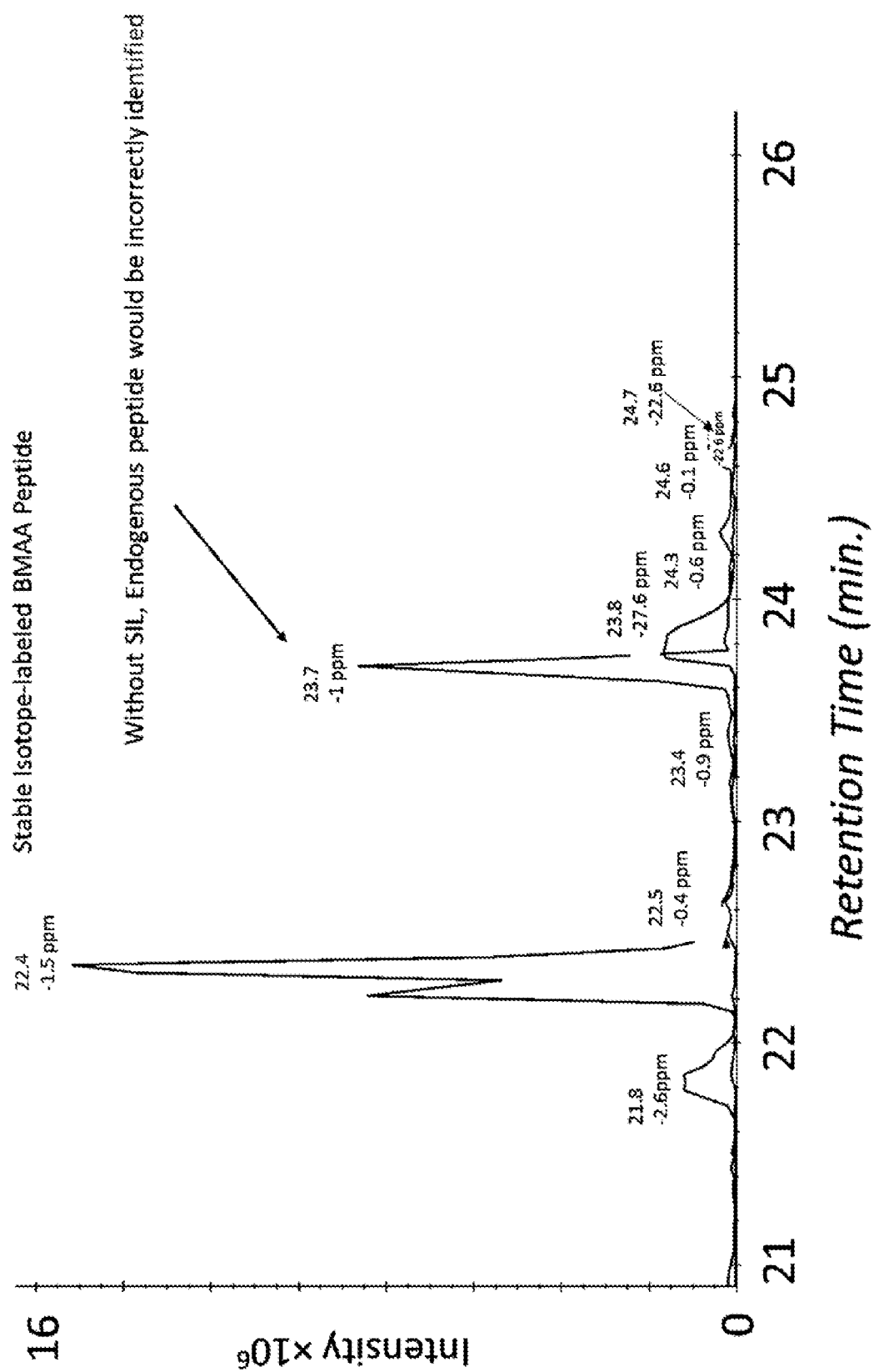
FIG. 7 is a plot showing that the elution time of SIL BMAA peptide is necessary for correct identification of endogenous peptide. Without this, the incorrect peak which is also within 5 ppm mass accuracy of the BMAA peptide of interest might be selected.
Figure 9:
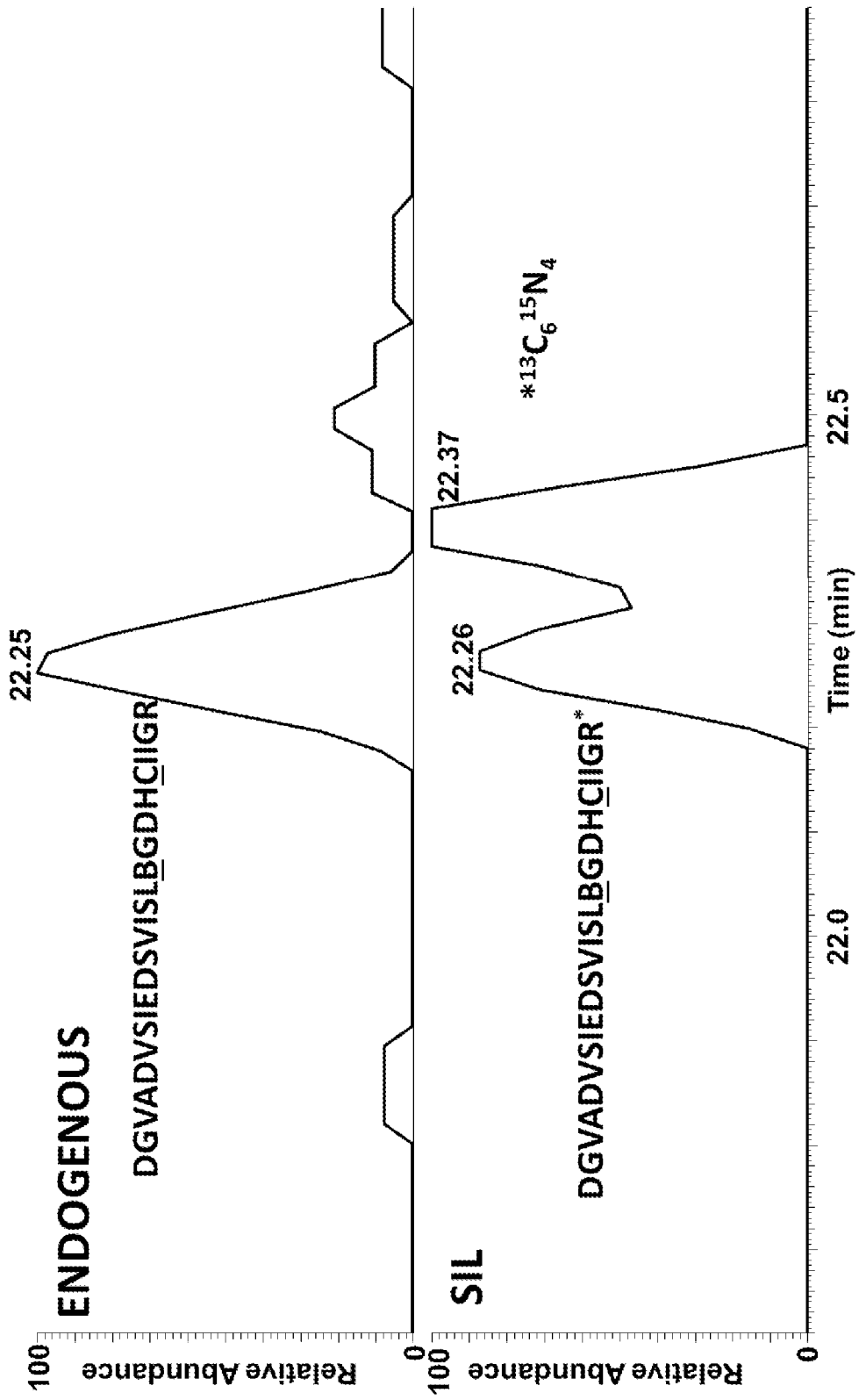
FIG. 9 is a plot illustrating the co-elution of endogenous and stable isotope-labeled BMAA containing peptides. Co-elution aids in confident identification.

Without the SIL BMAA peptide, correct identification of this peak becomes very difficult as other mass conflicts are present within 5 ppm of the endogenous BMAA peptide as shown in FIG. 7 where the most abundant peak is the same sequence does not co-elute with the SIL peptide. When examining the correct retention time, the intact mass appears to be present within 1.2 ppm mass accuracy and the correct charge state (+3) is also identified (FIG. 8). Moreover, this peak co-elutes with our SIL peptide as shown in FIG. 9. Fragment ions corresponding to the endogenous peptide with BMAA at the expected location could be identified at the same retention time (FIG. 10).

The compositions and methods of the appended claims are not limited in scope by the specific compositions and methods described herein, which are intended as illustrations of a few aspects of the claims. Any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A composition comprising an isotopically labeled compound defined by the formula below

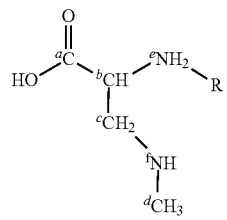

wherein R represents hydrogen or an amine protecting group; and
wherein at least four of $^aC$, $^bC$, $^cC$, $^dC$, $^eN$, and $^fN$, are isotopically labeled with a stable isotope.

2. The composition of claim 1, wherein $^aC$, $^bC$, $^cC$, $^dC$, $^eN$, and $^fN$ are isotopically labeled with a stable isotope.

3. The composition of claim 1, wherein the isotopically labeled compound is defined by the formula below

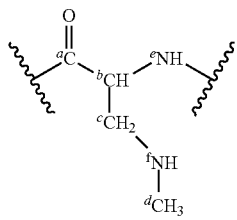

wherein R represents hydrogen or an amine protecting group;
wherein the $^{13}C$ isotopic enrichment factor for $^aC$, $^bC$, $^cC$, and $^dC$ is at least 25; and
wherein the $^{15}N$ isotopic enrichment factor for $^eN$ and $^fN$ is at least 100.

4. The composition of claim 3, wherein the $^{13}C$ isotopic enrichment factor for $^aC$, $^bC$, $^cC$, and $^dC$ is at least 80 and the $^{15}N$ isotopic enrichment factor for $^eN$ and $^fN$ is at least 200.

5. The composition of claim 1, wherein all eight of $^aC$, $^bC$, $^cC$, $^dC$, $^eN$, $^fN$, $^gO$, and $^hO$ are isotopically labeled with a stable isotope.

6. The composition of claim 1, wherein R is hydrogen.

7. The composition of claim 1, wherein R represents a 9-fluorenylmethyloxycarbonyl group.

8. The composition of claim 1, wherein the isotopically labeled compound is at least 0.5% by weight of the composition.

9. The composition of claim 1, wherein the isotopically labeled compound is $^{13}C_3{}^{15}N_2$ β-N-methylamino-L-alanine.

10. The composition of claim 1, wherein the isotopically labeled compound is defined by the formula below

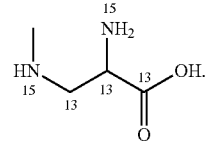

11. A method for quantifying the amount of β-N-methylamino-L-alanine (BMAA) in a sample comprising:
(i) analyzing a test sample by mass spectrometry;
(ii) spiking the test sample with a defined amount of the composition of claim 1;
(iii) analyzing the spiked sample by mass spectrometry; and
(iv) determining the amount of BMAA in the test sample by isotope dilution analysis.

* * * * *